(12) United States Patent  
Nakahama et al.

(10) Patent No.: US 7,507,383 B2
(45) Date of Patent: Mar. 24, 2009

(54) PHOTOCATALYTIC REACTION DEVICE

(75) Inventors: Takafumi Nakahama, Tokyo (JP); Kazuo Sato, Chiba-ken (JP); Kuniyuki Araki, Saitama-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 877 days.

(21) Appl. No.: 10/975,848

(22) Filed: Oct. 29, 2004

(65) Prior Publication Data

US 2005/0152812 A1 Jul. 14, 2005

(30) Foreign Application Priority Data

Oct. 31, 2003 (JP) ............................. P2003-371609
Mar. 30, 2004 (JP) ............................. P2004-099611

(51) Int. Cl.
*B01J 19/08* (2006.01)

(52) U.S. Cl. .................................... 422/186.3; 422/121

(58) Field of Classification Search ............. 422/186.3, 422/121
See application file for complete search history.

(56) References Cited

U.S. PATENT DOCUMENTS

| | | | |
|---|---|---|---|
| 4,892,712 A * | 1/1990 | Robertson et al. ........... 422/186 |
| 7,056,476 B2 * | 6/2006 | Okada et al. ................ 422/121 |
| 2002/0172628 A1 | 11/2002 | Segawa et al. | |
| 2003/0044326 A1 | 3/2003 | Yamasaki et al. | |
| 2004/0007000 A1 | 1/2004 | Takeda et al. | |

FOREIGN PATENT DOCUMENTS

| | | |
|---|---|---|
| EP | 1527809 B1 | 3/2007 |
| JP | 11-335187 | 12/1999 |
| JP | 2000-97452 | 4/2000 |
| JP | 2000-315420 | 11/2000 |
| JP | 2000-325446 | 11/2000 |
| JP | 2002-253662 | 9/2002 |
| JP | 2003-070888 A * | 3/2003 |
| JP | 2003-106581 | 4/2003 |
| JP | 2003-240285 | 8/2003 |
| JP | 2004-100585 | 4/2004 |
| JP | 2004-181301 | 7/2004 |

OTHER PUBLICATIONS

European Search Report issued by European Patent Office, dated Feb. 23, 2005, for European Patent Application No. EP 04 02 5764.

* cited by examiner

*Primary Examiner*—Kishor Mayekar
(74) *Attorney, Agent, or Firm*—Finnegan, Henderson, Farabow, Garrett & Dunner, L.L.P.

(57) ABSTRACT

An intake port (2) is formed in a casing (1), a plurality of discharge ports (3) are formed in a side face of the casing (1) different from this intake port (2), or are arranged continuously along the entire circumferential surface of the side face of the casing 1. A series of vanes (5) of a centrifugal type blower (4) for feeding air flowing in from the intake port 2 to the discharge ports (3) are arranged around the intake port (2) within the casing (1) and a photocatalyst carrier (6) that carries photocatalyst is arranged at the outer periphery of the series of vanes (5) of this centrifugal type blower (4).

6 Claims, 32 Drawing Sheets

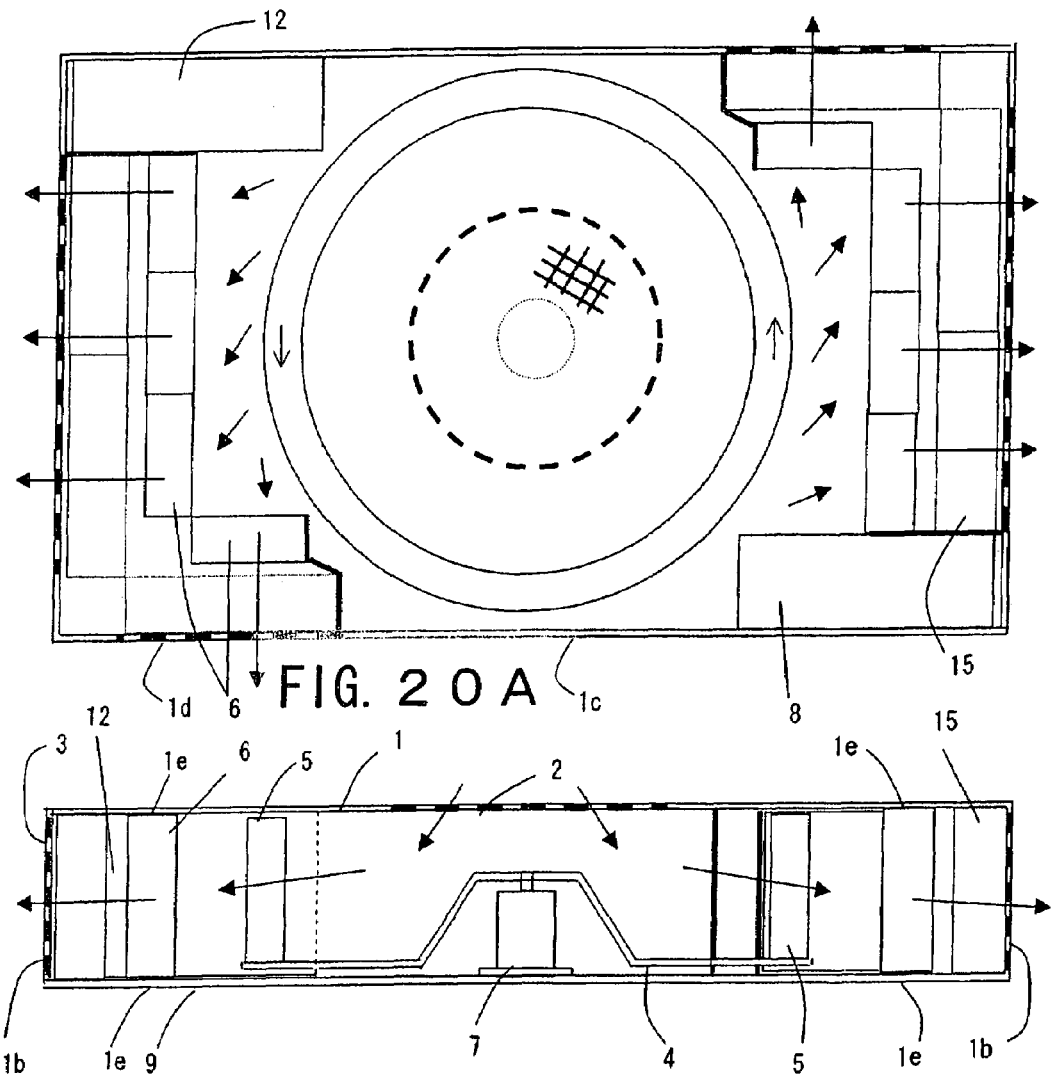

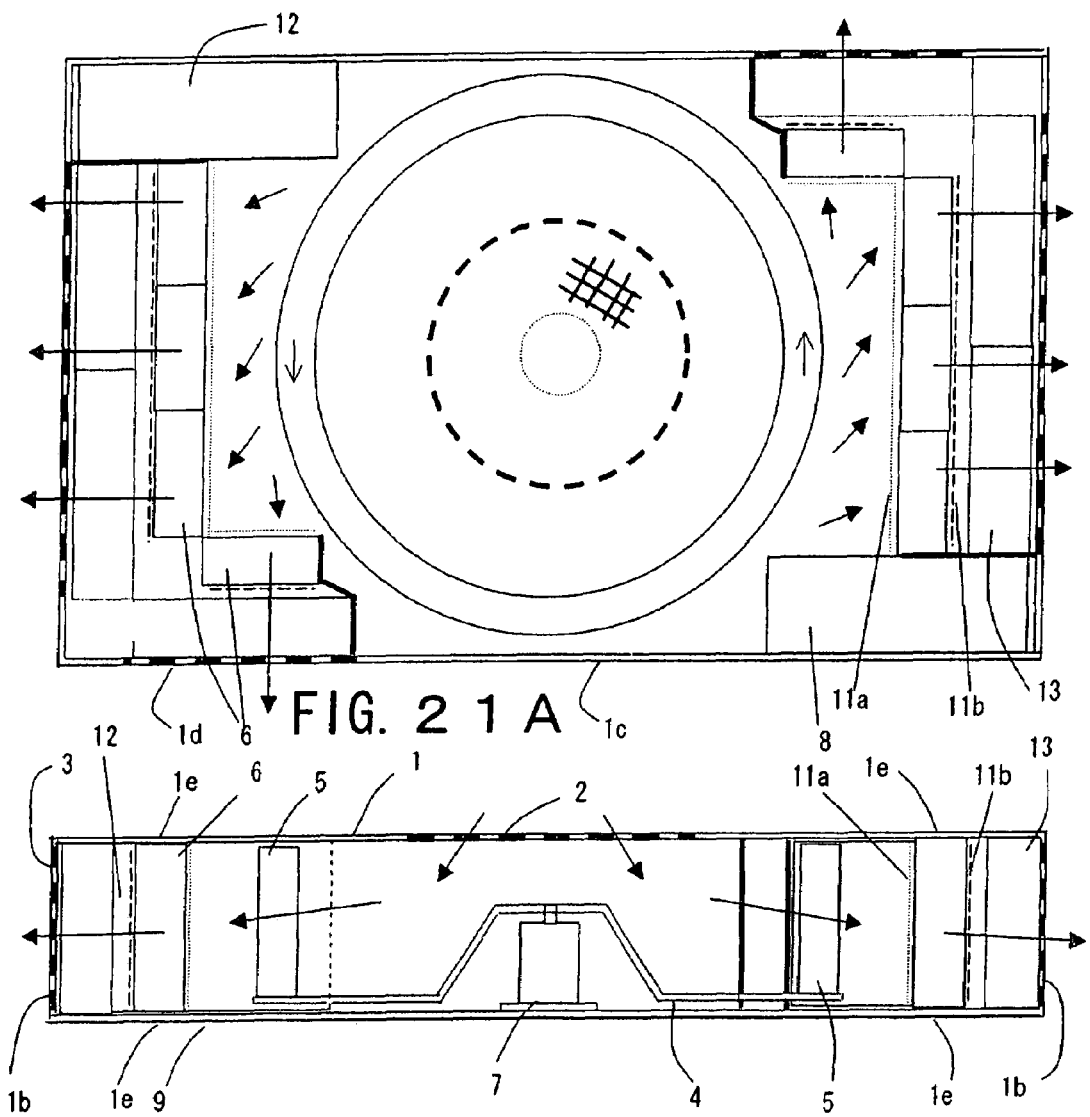

PHOTOCATALYTIC REACTION DEVICE

CROSS-REFERENCE TO RELATED APPLICATION

This application claims benefit of priority from Japanese Applications No. JP 2003-371609 filed 31Oct., 2003 and JP 2004-99611 filed 30 Mar. 2004, the entire contents of which are incorporated herein by reference.

BACKGROUND OF THE INVENTION

1. Field of the Invention

The present invention relates to a photocatalytic reaction device comprising a photocatalyst, a photocatalyst carrier that carries (or supports) this photocatalyst and a blower (an air blower), whereby substances that come into contact with, adhere to or approach the photocatalyst are decomposed by a photocatalytic reaction.

2. Description of the Related Art

Devices for cleaning air (or purifying air), comprising a dust collecting filter or deodorizing filter and a blower, are well known. An example is the device disclosed in Laid-open Japanese Patent Application No. Tokkai 2003-106581. A photocatalyst and a photocatalyst carrier that carries this photocatalyst are also known, an example being Laid-open Japanese Patent Application No. Tokkai H. 11-335187.

Photocatalytic reaction devices are also already known comprising a photocatalyst, a photocatalyst carrier made of a porous substance that carries this photocatalyst, and a blower, wherein substances coming into contact with, adhering to or approaching the photocatalyst are decomposed by a photocatalytic reaction.

A prior art of such a photocatalytic reaction device is shown in FIG. 1A and FIG. 1B. In these Figures, the lower Figure (FIG. 1B) shows a cross-sectional view including the axis (axis center) of a series of blower vanes, and the upper Figure (FIG. 1A) shows a cross-section in the direction perpendicular to the aforementioned axis, including the blower drive motor. The cross-section of the hub of the blower is not shown in the upper Figure (FIG. 1A).

In the photocatalytic reaction device 9 shown in FIG. 1A and FIG. 1B, fluid that flows in from an intake port (inlet port, suction port) 2 provided in the casing 1 flows out from a discharge port 3 arranged in the face where the intake port 2 is provided, or in a location in a face other than this. A centrifugal type blower 4 is provided, having a series of vanes 5, in the vicinity of the intake port 2 inside the casing 1 and a photocatalyst carrier 6 that carries a photocatalyst is provided at the discharge port. A blower drive motor 7 and a motor power source 8 are provided within the casing 1. In this photocatalytic reaction device 9, substances in the air coming into contact with, adhering to or approaching the catalyst carried on the photocatalyst carrier 6, such as for example impurities, are decomposed by a reaction such as oxidation or reduction.

Also, high voltage from a high-voltage power source 12 shown in these Figures is applied to high-voltage terminals 11a, 11b arranged on the upstream side and downstream side of the photocatalyst carrier 6 and electrical discharge is produced between these two terminals. Ultraviolet light is thereby generated, that promotes the decomposition action of the photocatalyst. Impurities in the air undergo oxidative decomposition by the ozone that is then generated by the ultraviolet light. Ozone that is not used in this decomposition is absorbed by an ozone decomposition filter 13 arranged on the inside of the discharge port 3.

In a prior art photocatalytic reaction device, as shown by the characteristic plot of FIG. 32, the airflow resistance of the photocatalyst carrier 6 and ozone decomposition filter 13 is R0, the external diameter of the series of vanes 5 of the centrifugal type blower 4 arranged on the internal diameter side of the photocatalyst carrier 6 is small and a partition 20 is present, so the fan performance is C0. This therefore resulted in the problem that the flow rate was small, at Q0, with the result that treatment of impurities present in the air in large quantity could not be achieved.

Also, the series of vanes 5 generates fluid noise, but, as shown in FIG. 1A and FIG. 1B, the photocatalyst carrier 6 and ozone decomposition filter 13 are arranged on the side of the discharge port 3, so noise is attenuated and the noise propagated to the outside from the discharge port 3 can thereby be reduced. However, there was the problem that noise from the intake port 2 was propagated to the outside with scarcely any attenuation.

SUMMARY OF THE INVENTION

Accordingly, one object of the present invention is to provide a novel photocatalytic reaction device having a high decomposition treatment capability so as to be capable of treating impurities present in the air in large quantity.

A further object of the present invention is to provide a photocatalytic reaction device of low noise.

In order to achieve the foregoing objects, a photocatalytic reaction device according to the present invention is constructed as follows. Specifically, a photocatalytic reaction device according to the present invention comprises an intake port formed in a casing, discharge ports formed in a side face of the casing different from this intake port, a centrifugal type blower for feeding fluid flowing in from the intake port to the discharge ports, and a photocatalyst carrier that carries photocatalyst and is provided in the fluid path between the intake port and the discharge ports, wherein the discharge ports are formed over the entire surface of the side face of the casing or are formed in a plurality of locations of the side face of the casing.

It is also possible to adopt a construction wherein the photocatalyst carrier is provided around the intake port, the series of vanes of the centrifugal type blower is provided at the outer periphery of the photocatalyst carrier, and ozone decomposition filters are provided at the outer periphery of the series of vanes of the centrifugal type blower.

It is also possible to adopt a construction wherein the photocatalyst carrier is provided facing the intake port, the series of vanes of the centrifugal type blower is arranged facing the opposite side of this photocatalyst carrier 6 to that of the intake port and ozone decomposition filters are provided at the outer periphery of the series of vanes of the centrifugal type blower.

With the present invention, a photocatalytic reaction device can be provided having a high decomposition treatment capability, that is capable of treating impurities present in large quantity in air.

Also, noise can be reduced by adopting a construction wherein the photocatalyst carrier is provided around the intake port and the series of vanes of the centrifugal type blower is provided at the outer periphery of the photocatalyst carrier, or the photocatalyst carrier is provided facing the intake port and the series of vanes of the centrifugal type blower is arranged facing the opposite side of this photocatalyst carrier to that of the intake port and ozone decomposition filters are provided at the outer periphery of the series of vanes of the centrifugal type blower.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 20A and FIG. 20B are cross-sectional views showing the construction of a photocatalytic reaction device according to a nineteenth embodiment of the present invention;

FIG. 21A and FIG. 21B are cross-sectional views showing the construction of a photocatalytic reaction device according to a twentieth embodiment of the present invention;

DETAILED DESCRIPTION OF THE PREFERRED EMBODIMENTS

Figure 1:
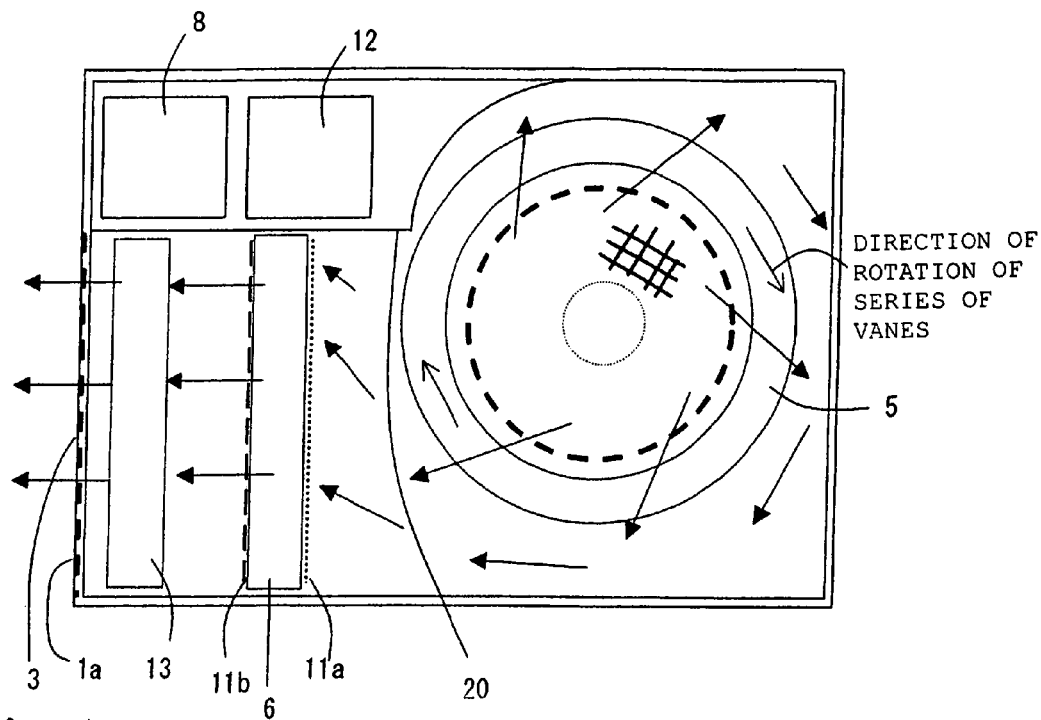
FIG. 1A and FIG. 1B are cross-sectional views showing the construction of a prior art device (a conventional device)
Figure 1:
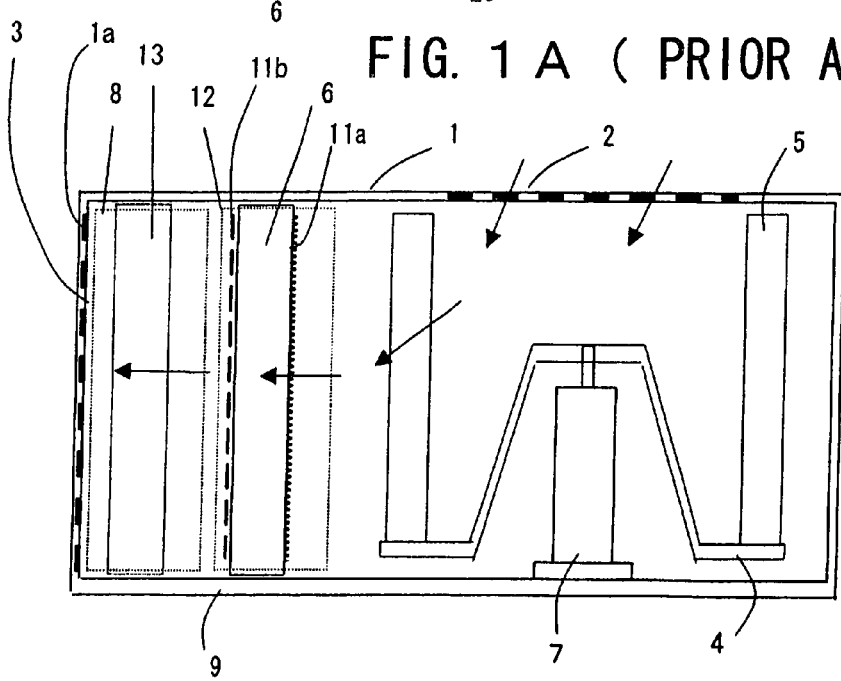

Referring now to the drawings, wherein like reference numerals designate identical or corresponding parts throughout the several views, and more particularly to FIG. 2A and FIG. 2B thereof, one embodiment of the present invention will be described.

In the following Figures, symbols that are identical with those used in FIG. 1A and FIG. 1B indicate the same or corresponding parts.

In the following Figures showing the construction of photocatalyst reaction devices according to various embodiments, the lower Figures (FIGS. B) show a cross-section containing the axis of the series of vanes of the blower while the upper Figures (FIGS. A) show a cross-section in the direction perpendicular to the aforesaid axis, containing the blower drive motor. The cross-section of the hub of the blower is not shown in the upper Figures (FIGS. A).

First Embodiment

Figure 2A:
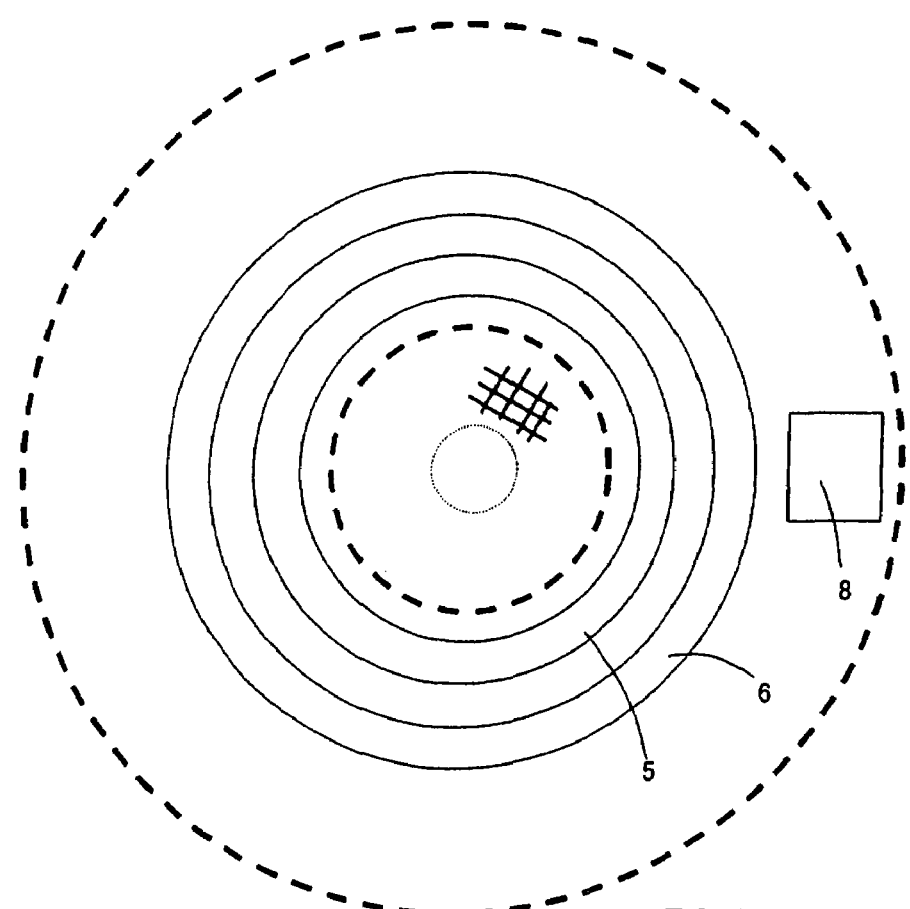
FIG. 2A and FIG. 2B are cross-sectional views showing the construction of a photocatalytic reaction device according to a first embodiment of the present invention.
Figure 2B:
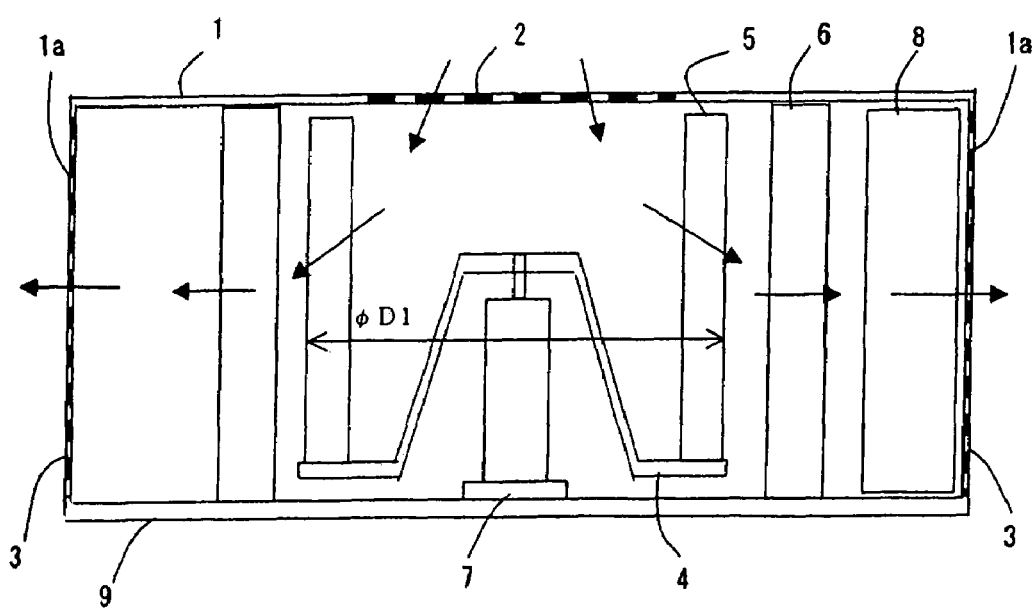

FIG. 2A and FIG. 2B are views showing the construction of a photocatalytic reaction device according to a first embodiment of the present invention.

In the photocatalytic reaction device 9 of this embodiment, an intake port 2 having apertures in the form of a mesh is formed in the middle of the upper surface of a cylindrical casing 1. Also, a plurality of discharge ports 3 having apertures in the form of a mesh are formed in a side face of the casing 1 different from that in which this intake port 2 is formed. Also, a series of vanes 5 of a centrifugal type blower 4 for delivering air flowing in from the intake port 2 to the discharge ports 3 is arranged around the intake port 2 within the casing 1 and an annular photocatalyst carrier 6 made of a porous body that carries a photocatalyst is arranged at the outer periphery of the series of vanes 5 of this centrifugal type blower 4. A construction is adopted in which the discharge ports 3 are arranged on the side face of the casing 1 of the photocatalytic reaction device 9, at least two discharge ports being arranged in directions differing by practically 180° in the radial direction of the series of vanes 5 of the centrifugal type blower 4, or a plurality of discharge ports being arranged around the centrifugal type blower 4, or the discharge ports being arranged continuously over the entire periphery of the side face of the casing 1.

Figure 32:
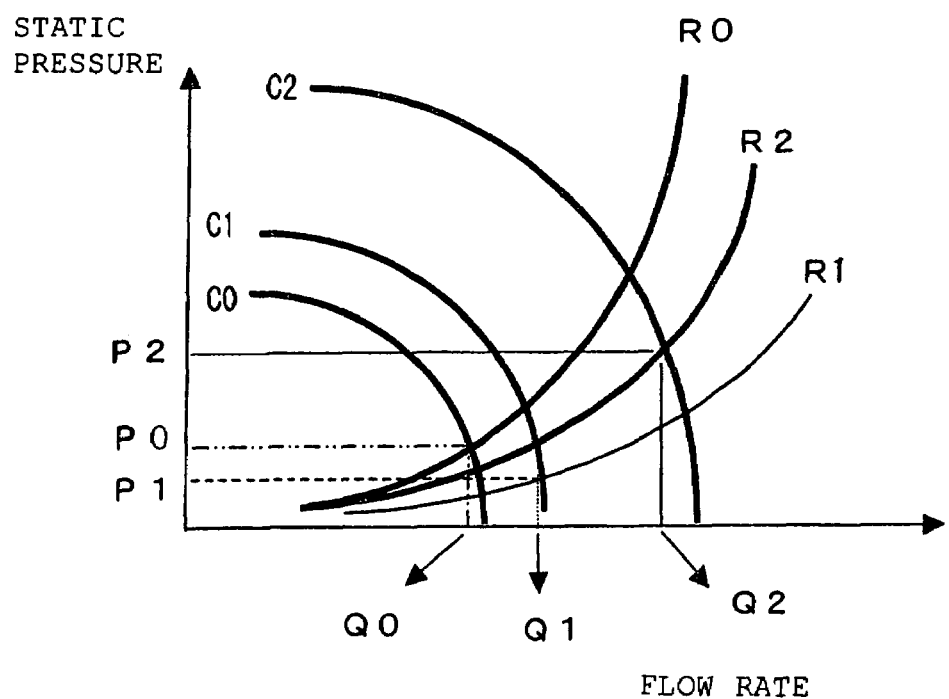
FIG. 32 is a view showing the static pressure-flow rate characteristic of a centrifugal type blower and the airflow resistance of the device in a prior art device and a device according to an embodiment of the present invention.

In the construction of this embodiment, the partition 20 that was conventionally provided in the vicinity of the series of vanes 5 is absent, so that, as shown in FIG. 32, the fan characteristic is shifted from C0 to a characteristic C1 providing a large flow rate and a large static pressure. Also, due to increase of the area of the flow paths to the discharge ports 3, the airflow resistance is decreased from R0 to R1. As a result, the operating flow rate increases to Q1 from the conventional value of Q0 so that a higher decomposition treatment capability than conventionally is displayed in respect of impurities in the air.

Second Embodiment

Figure 3:
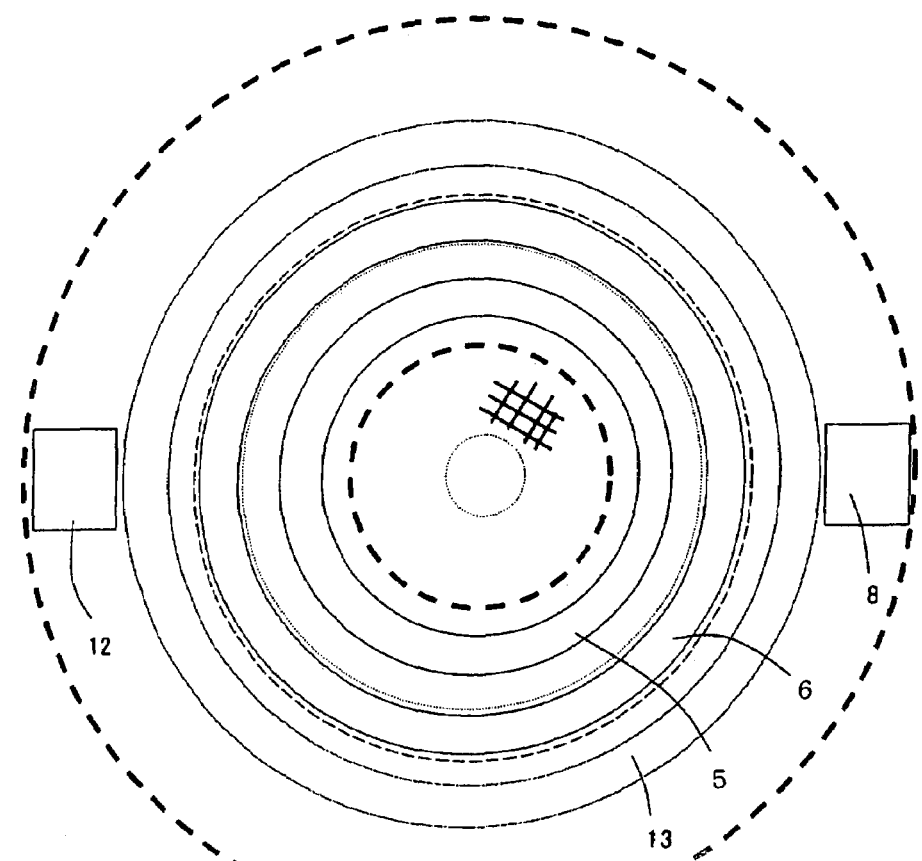
FIG. 3A and FIG. 3B are cross-sectional views showing the construction of a photocatalytic reaction device according to a second embodiment of the present invention.
Figure 3:
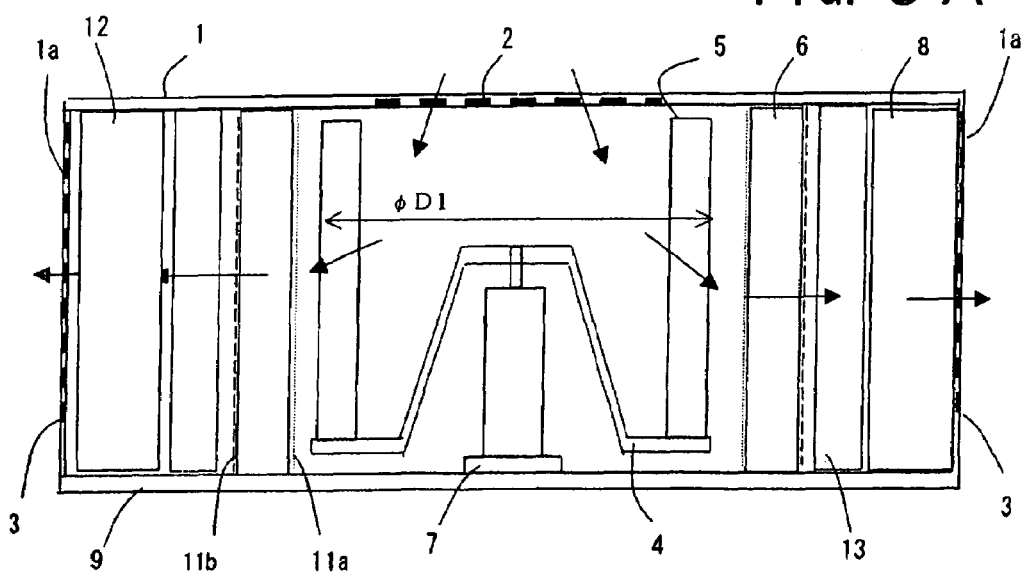

FIG. 3A and FIG. 3B are views showing the construction of a photocatalytic reaction device according to a second embodiment of the present invention.

A photocatalytic reaction device according to this second embodiment has a construction wherein, in the first embodiment described above, high-voltage terminals 11a, 11b connected with a high-voltage power source 12 are arranged at the outer periphery and inner periphery of the photocatalyst carrier 6 and ozone decomposition filters 13 are arranged on the side of these nearest the discharge ports 3.

The decomposition effect of the photocatalyst is increased by the generation of ultraviolet light by discharge between the high-voltage terminals 11a, 11b. The high-voltage terminals 11a, 11b constitute ultraviolet ray generating means (generating unit).

The ozone that is generated by this ultraviolet light then performs oxidative decomposition of impurities in the air. Ozone that is not used for this decomposition is absorbed by ozone decomposition filters 13. As a result, since there is no outflow of excess ozone from the discharge ports 3, sufficient ozone to decompose the impurities in the air can be generated, so that the device according to this embodiment shows a decomposition treatment capability higher than that of the photocatalytic reaction device of the first embodiment, described above.

Third Embodiment

Figure 4:
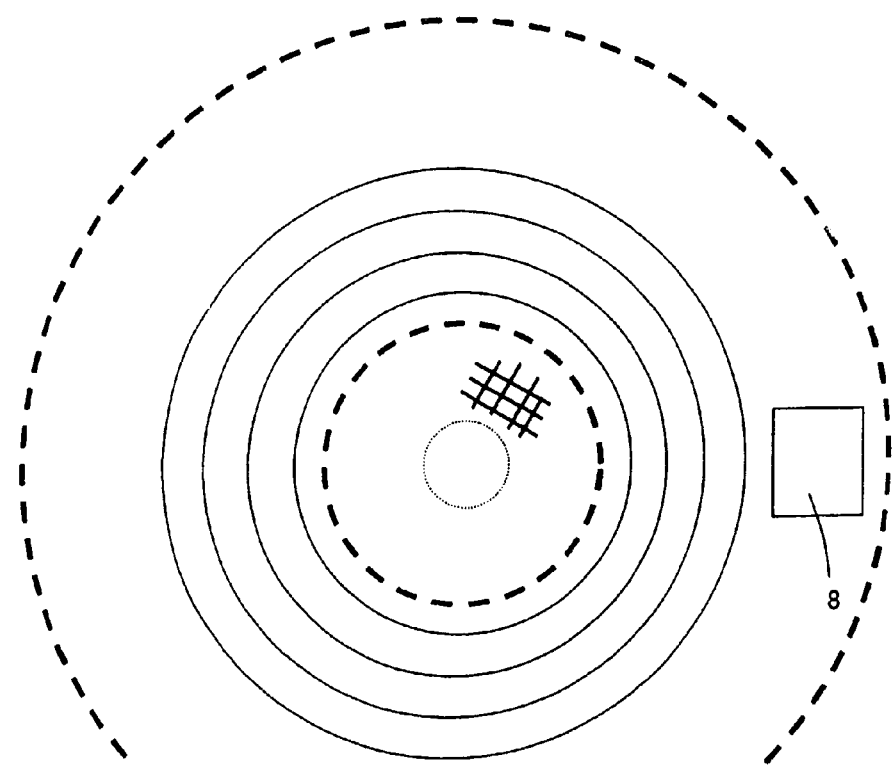
FIG. 4A and FIG. 4B are cross-sectional views showing the construction of a photocatalytic reaction device according to a third embodiment of the present invention.
Figure 4:
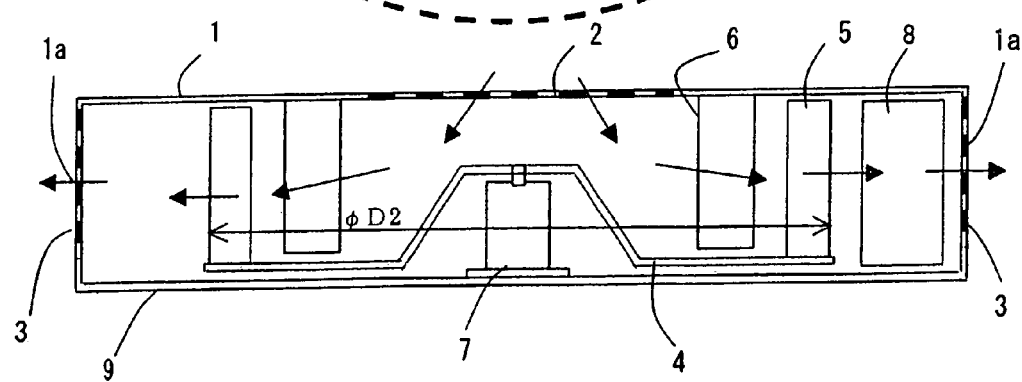

FIG. 4A and FIG. 4B are views showing the construction of a photocatalytic reaction device according to a third embodiment of the present invention.

In the first and second embodiment described above, the photocatalyst carrier 6 was arranged at the outer periphery of the series of vanes 5 of the centrifugal type blower 4, but, in this third embodiment, the photocatalyst carrier 6 carrying the photocatalyst is arranged around the intake port 2 within the casing 1 and the series of vanes 5 of the centrifugal type blower 4 is arranged at the outer periphery of the photocatalytic reaction photocatalyst carrier 6.

Figure 5:
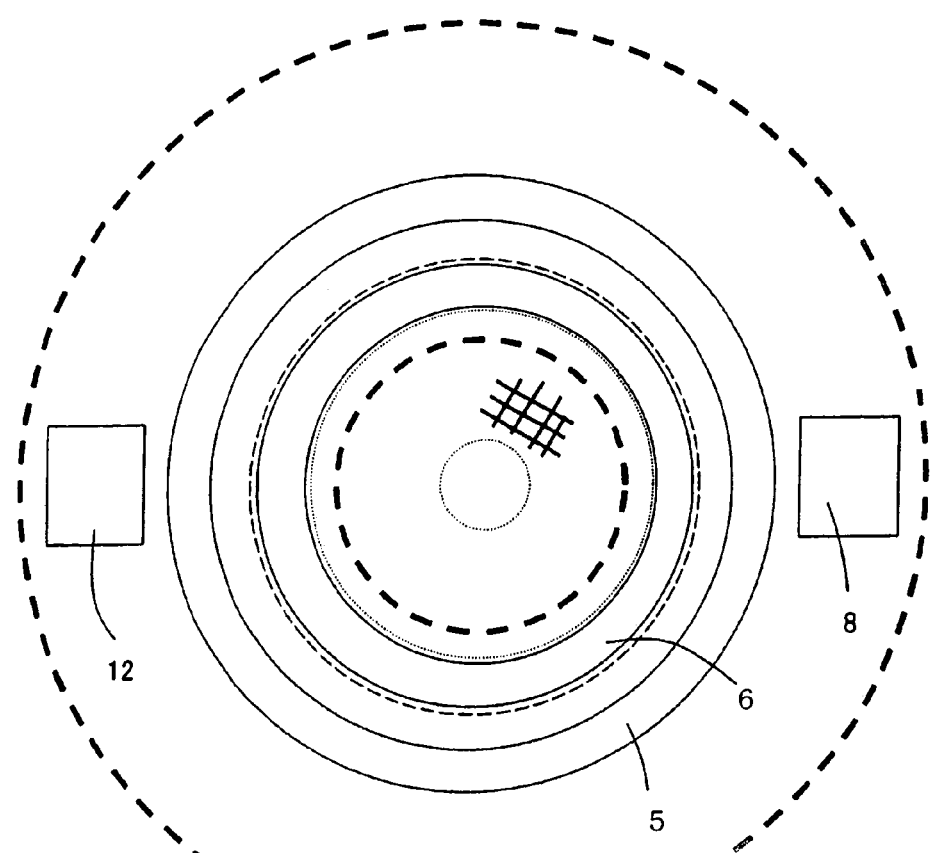
FIG. 5A and FIG. 5B are cross-sectional views showing the construction of a photocatalytic reaction device according to a fourth embodiment of the present invention.
Figure 5:
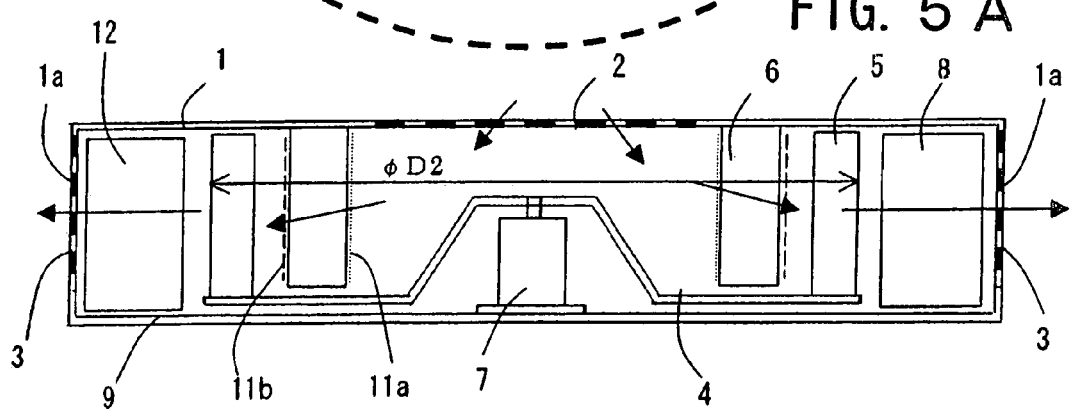

In this way, by arranging the series of vanes 5 of the centrifugal type blower 4 at the outer periphery of a photocatalyst carrier 6, the external diameter of the series of vanes 5 can be increased compared with the prior art construction, in which the series of vanes 5 of the centrifugal type blower 4 was arranged at the inner periphery of the photocatalyst carrier 6 (i.e. $\phi D2 > \phi D1$), resulting in a fan characteristic C2 providing a large static pressure. Also, in order to make the photocatalyst carrier 6 of the same volume as conventionally, the photocatalyst carrier 6 is arranged at the inner periphery of the series of vanes 5, the diameter of the photocatalyst carrier 6 being made smaller, while its thickness is made larger; thus the airflow resistance is increased from R1 to R2. The flow rate Q2 is thereby increased from the flow rate Q1 of the first embodiment and a decomposition treatment capability for impurities in the air is thereby displayed that is higher than that of the first embodiment Fourth Embodiment FIG. 5A and FIG. 5B are views showing the construction of a photocatalytic reaction device according to a fourth embodiment of the present invention.

A photocatalytic reaction device according to this fourth embodiment has a construction wherein, in a photocatalytic reaction device according to the third embodiment described above, high-voltage terminals 11a, 11b connected with a high-voltage power source 12 are arranged at the outer periphery and inner periphery of the photocatalyst carrier 6.

Ultraviolet light is generated by discharge between the high-voltage terminals 11a, 11b. As a result, the photocatalytic reaction is promoted and a higher decomposition treatment capability for impurities in the air is displayed than in the case of the third embodiment.

Fifth Embodiment

Figure 6:
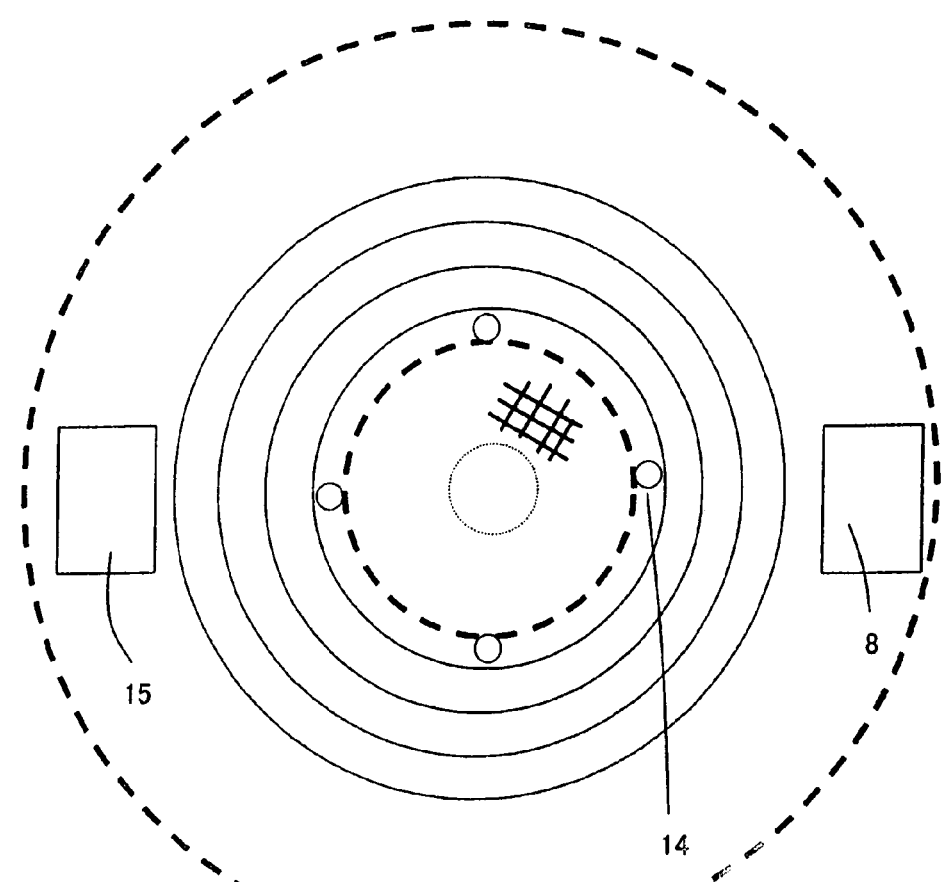
FIG. 6A and FIG. 6B are cross-sectional views showing the construction of a photocatalytic reaction device according to a fifth embodiment of the present invention.
Figure 6:
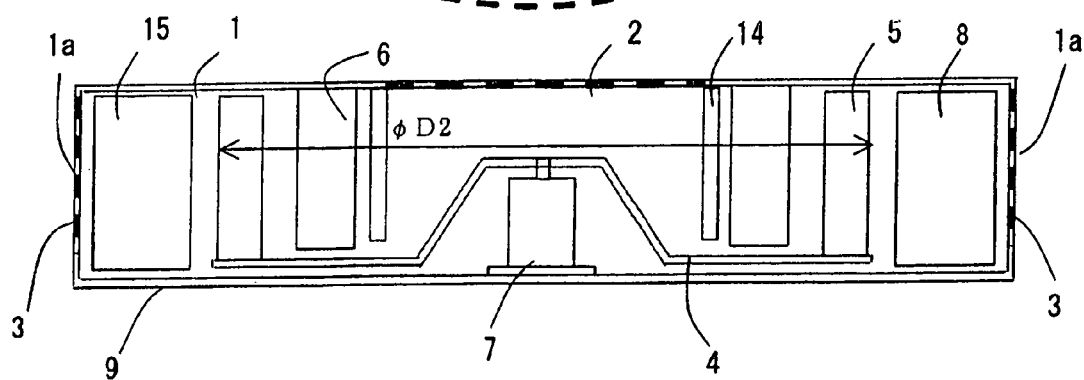

FIG. 6A and FIG. 6B are views showing the construction of a photocatalytic reaction device according to a fifth embodiment of the present invention.

A photocatalytic reaction device according to this fifth embodiment has a construction wherein, in a photocatalytic reaction device according to the third embodiment described above, ultraviolet lamps 14 are arranged at the inner periphery of the photocatalyst carrier 6.

Ultraviolet light is directed onto the photocatalyst of the photocatalyst carrier 6 by arranging the ultraviolet lamps 14 at the inner periphery of the photocatalyst carrier 6. As a result, the photocatalytic reaction is promoted and a higher decomposition treatment capability for impurities in the air is displayed than in the case of the third embodiment.

Sixth Embodiment

Figure 7A:
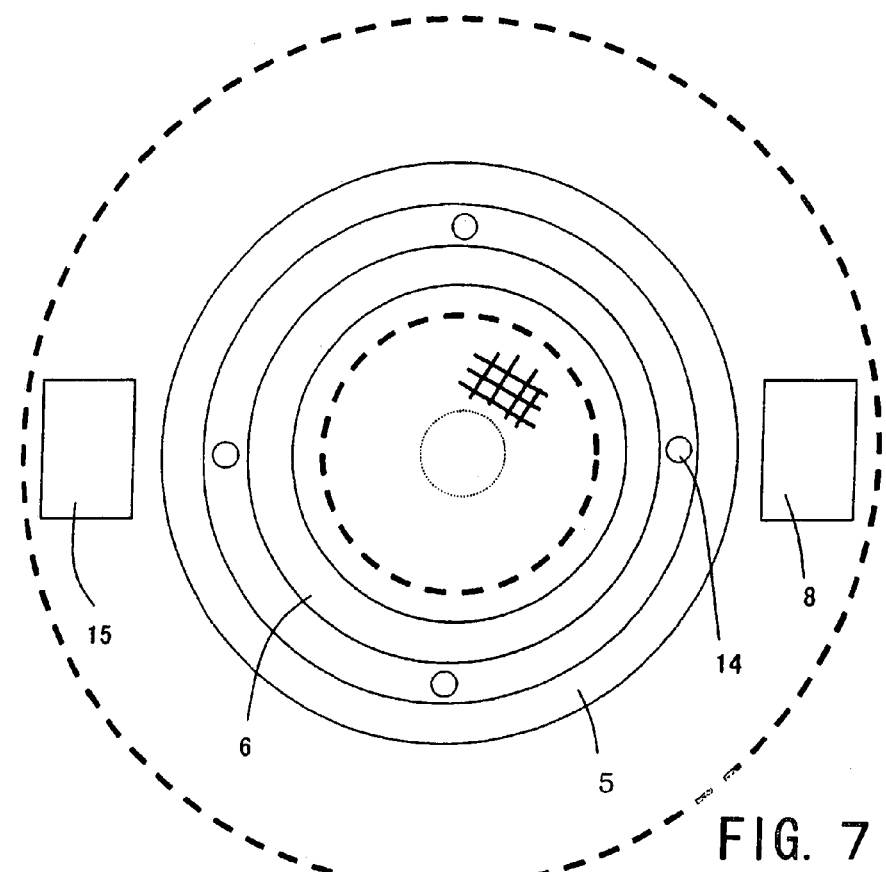
FIG. 7A and FIG. 7B are cross-sectional views showing the construction of a photocatalytic reaction device according to a sixth embodiment of the present invention.
Figure 7B:
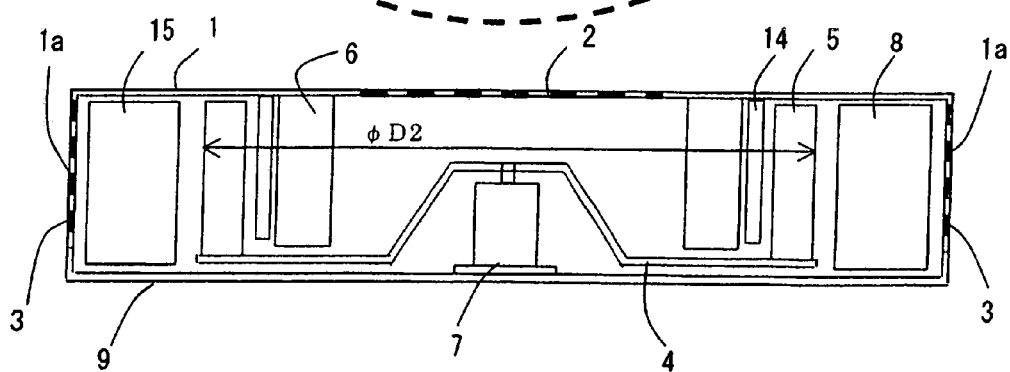

FIG. 7A and FIG. 7B are views showing the construction of a photocatalytic reaction device according to a sixth embodiment of the present invention.

A photocatalytic reaction device according to this sixth embodiment has a construction wherein, in a photocatalytic reaction device according to the third embodiment described above, ultraviolet lamps 14 are arranged at the outer periphery of the photocatalyst carrier 6.

Ultraviolet light is directed onto the photocatalyst of the photocatalyst carrier 6 by arranging the ultraviolet lamps 14 at the outer periphery of the photocatalyst carrier 6. In addition, ultraviolet light reflected at the surface of the series of vanes 5 arranged around the ultraviolet lamps 14 is directed onto the photocatalyst. As a result, the photocatalytic reaction is promoted and a higher decomposition treatment capability for impurities in the air is displayed than in the case of the third embodiment.

Seventh Embodiment

Figure 8:
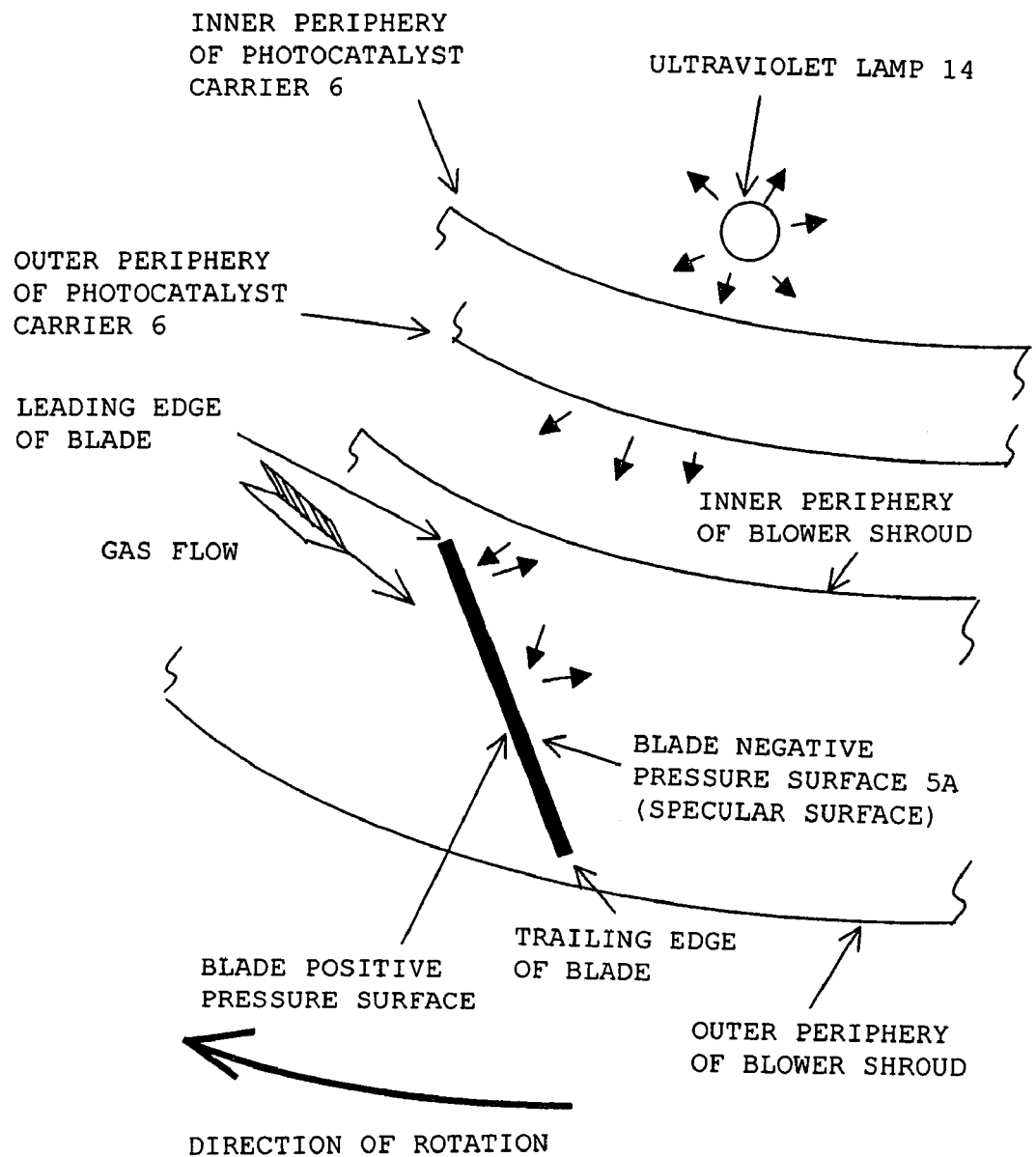
FIG. 8 is a view given in explanation of the construction of major parts of a photocatalytic reaction device according to a seventh embodiment of the present invention.

FIG. 8 is a view given in explanation of the construction of major parts of a photocatalytic reaction device according to a seventh embodiment of the present invention.

A photocatalytic reaction device according to this seventh embodiment has a construction wherein, in a photocatalytic reaction device according to the fifth embodiment described above, the negative pressure surfaces of the series of vanes 5 of the centrifugal type blower 4 are specular surfaces.

In this way, by making the negative pressure surfaces 5*a* of the series of vanes 5 of the centrifugal type blower 4 specular surfaces, ultraviolet light leaking from the outer peripheral side of the photocatalyst carrier 6 constituted by a porous body is reflected by the negative pressure surfaces 5*a* of the blades and is directed onto the photocatalyst carrier 6.

As a result, the photocatalytic reaction is promoted and a higher decomposition treatment capability for impurities in the air is displayed than in the case of the fifth embodiment.

Eighth Embodiment

Figure 9:
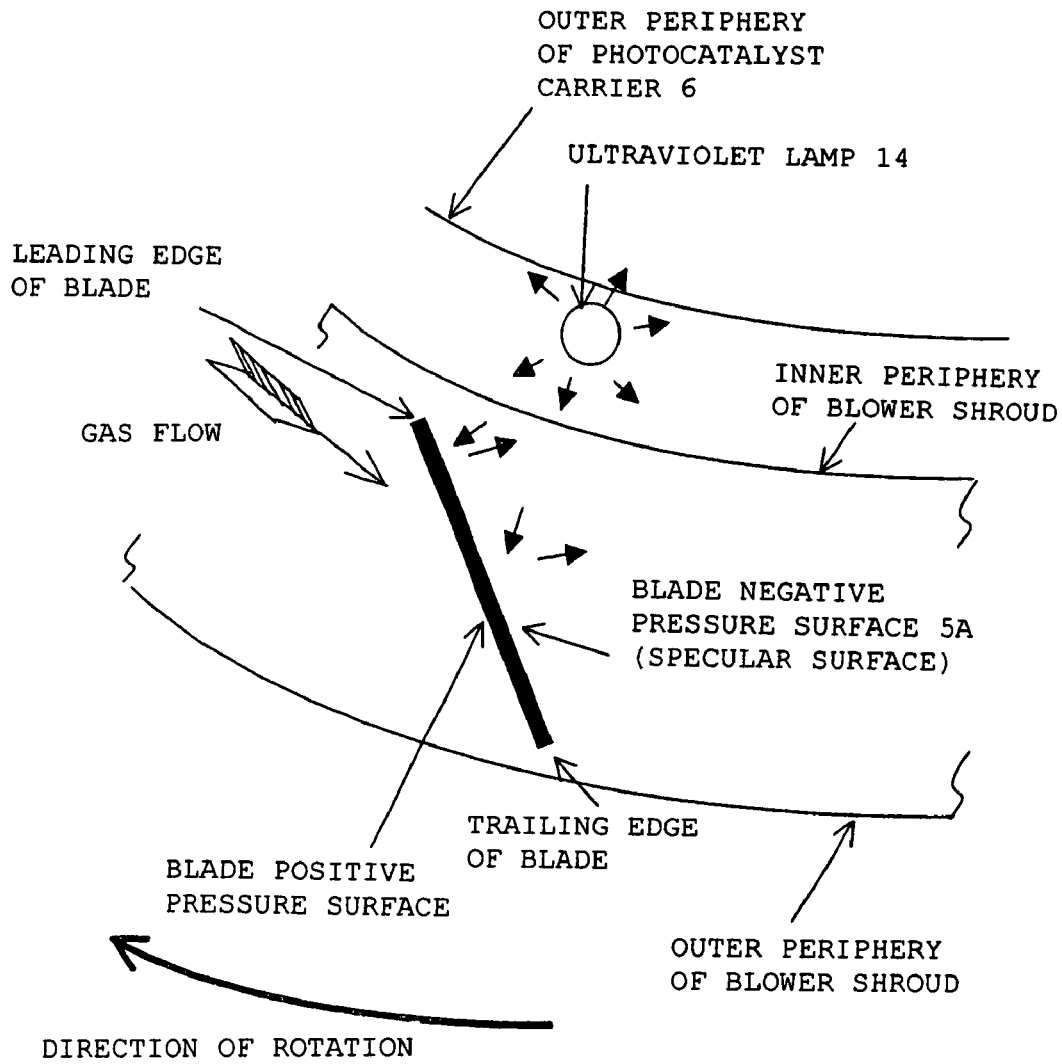
FIG. 9 is a view given in explanation of the construction of major parts of a photocatalytic reaction device according to an eighth embodiment of the present invention.

FIG. 9 is a view given in explanation (an explanation view) of the construction of major parts of a photocatalytic reaction device according to an eighth embodiment of the present invention.

A photocatalytic reaction device according to this eighth embodiment has a construction wherein, in a photocatalytic reaction device according to the sixth embodiment described above, the negative pressure surfaces of the series of vanes 5 of the centrifugal type blower 4 are specular surfaces.

In this way, by making the negative pressure surfaces 5*a* of the series of vanes 5 of the centrifugal type blower 4 specular surfaces, ultraviolet light directed towards the outer periphery from the ultraviolet lamps 14 is reflected by the negative pressure surfaces 5*a* of the blades and is directed onto the photocatalyst carrier 6.

As a result, the photocatalytic reaction is promoted and a higher decomposition treatment capability for impurities in the air is displayed than in the case of the sixth embodiment.

Ninth Embodiment

Next a photocatalytic reaction device according to a ninth embodiment of the present invention will be described. This photocatalytic reaction device according to the ninth embodiment has a construction wherein, in a photocatalytic reaction device according to the any of the fourth to eighth embodiments described above, ozone decomposition filters 13 are arranged at the outer periphery of the series of vanes 5 of the centrifugal type blower 4 and at the inner periphery of the discharge ports 3.

Figures 10A, 10B:
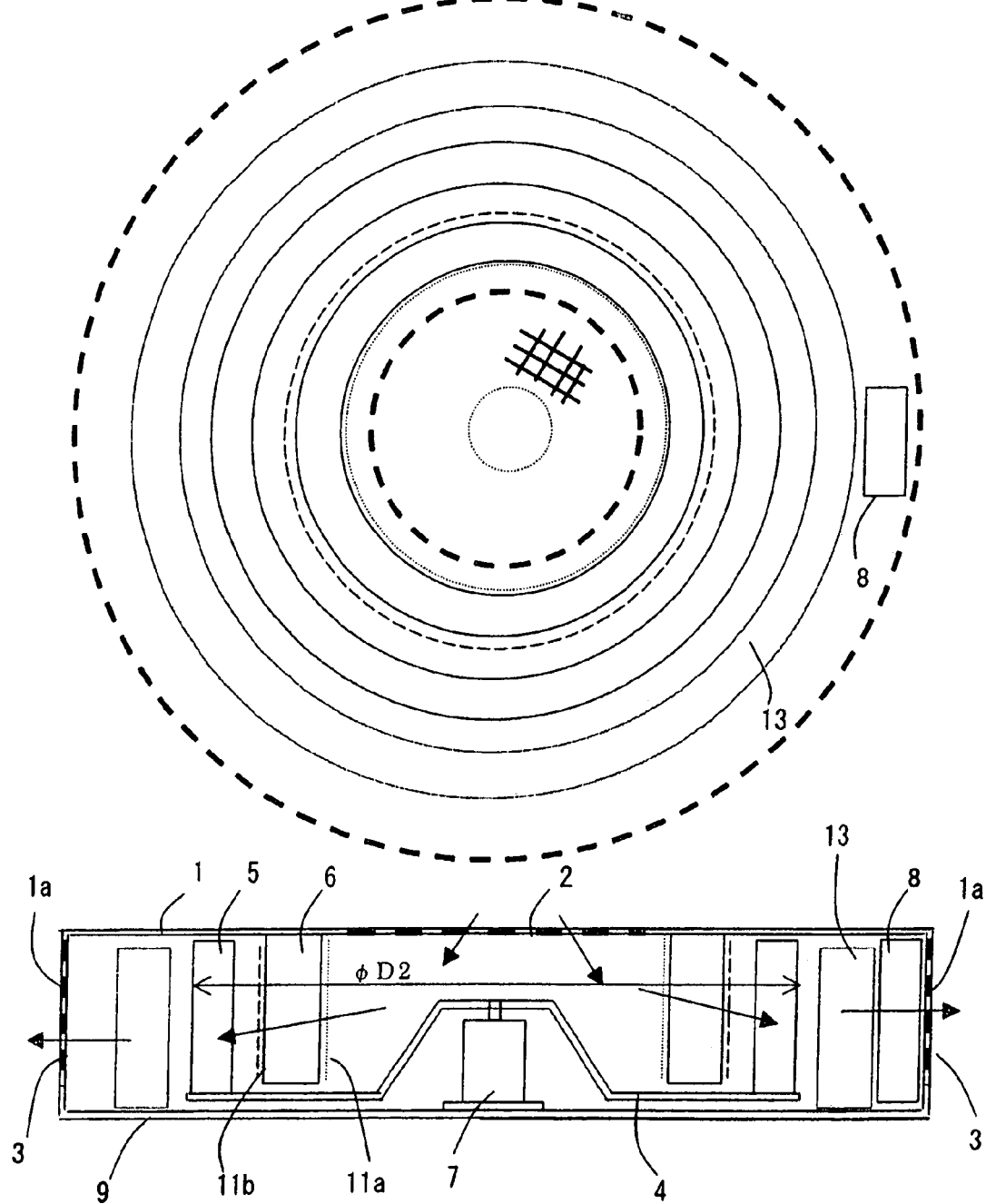
FIG. 10A and FIG. 10B are cross-sectional views showing the construction of a photocatalytic reaction device according to a ninth embodiment of the present invention.

FIG. 10A and FIG. 10B are views showing an example of the construction of this ninth embodiment.

By arranging the ozone decomposition filters 13 at the outer periphery of the series of vanes 5 of the centrifugal type blower 4, any ozone generated by the ultraviolet rays that was not used for decomposition is absorbed by the ozone decomposition filters 13 arranged at the inner periphery of the discharge ports 3. Since there is no outflow of excess ozone from the discharge ports 3, sufficient ozone to decompose the impurities in the air can be generated, so that the device according to this embodiment shows a decomposition treatment capability higher than that of the photocatalytic reaction device of the fourth to the eighth embodiments, described above.

Also, although the series of vanes 5 generates fluid noise, noise is attenuated by the arrangement of the photocatalyst carrier 6 at the inner periphery and the ozone decomposition filters 13 at the outer periphery, so the noise that is propagated to outside the casing 1 can be reduced.

Tenth Embodiment

Figure 11A:
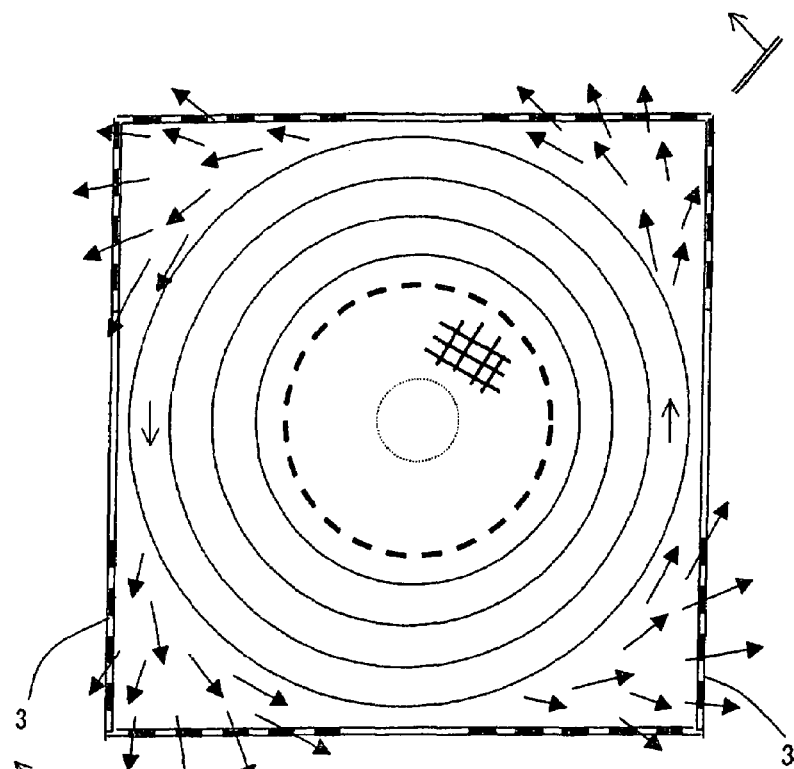
FIG. 11A and FIG. 11B are cross-sectional views showing the construction of a photocatalytic reaction device according to a tenth embodiment of the present invention.
Figure 11B:
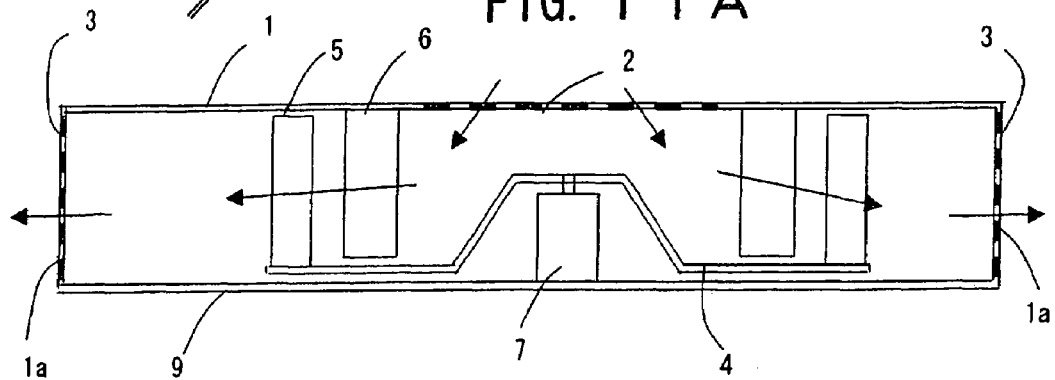

FIG. 11A and FIG. 11B are views showing the construction of a photocatalytic reaction device according to a tenth embodiment of the present invention. In these Figures, the lower Figure is a view showing a cross-section viewed in the direction of the arrows at the position of a diagonal of a practically square casing 1 in the upper Figure.

Instead of being circular, as in the third embodiment described above, the shape of the casing of the photocatalytic reaction device of this tenth embodiment is practically square, when seen in projection from a direction perpendicular to the intake port, and the discharge ports 3 are arranged at the corners of this practically square casing.

Due to the casing 1 being practically square in projection from a direction perpendicular with respect to the intake port 2 and the discharge ports 3 being arranged at the corners of this practically square casing 1, the air pressure at the corners is raised by air flowing out from the series of vanes 5, enabling the air to flow out smoothly from the discharge ports 3. As a result, in spite of the practically square shape of the casing 1 of smaller area in projection in the axial direction of the casing 1 compared with the third embodiment, due to the smaller airflow resistance, the flow rate is practically unchanged and the device therefore shows a decomposition treatment capability in respect of impurities in the air that is on the same level with that of the third embodiment.

Eleventh Embodiment

Figure 12A:
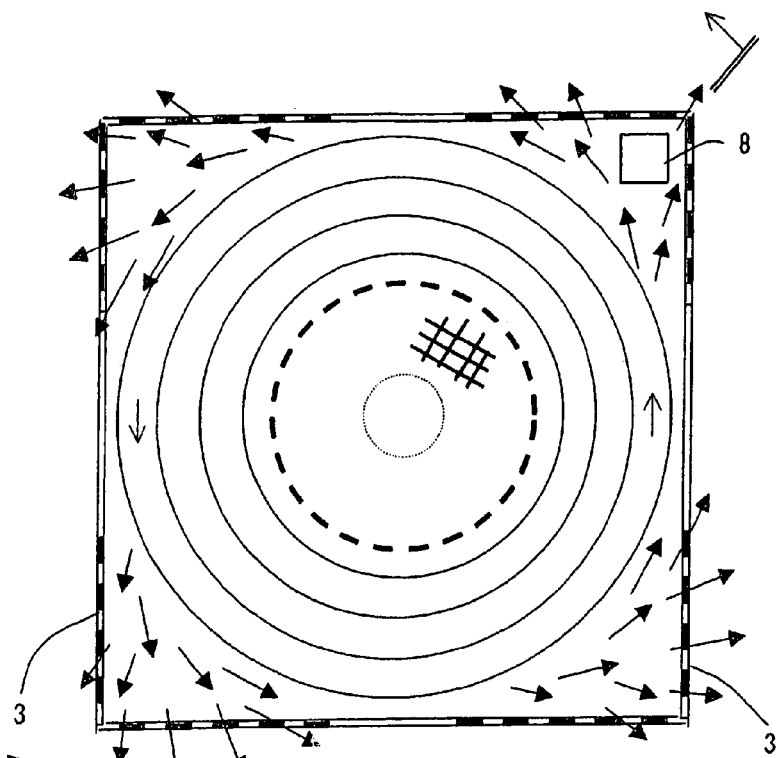
FIG. 12A and FIG. 12B are cross-sectional views showing the construction of a photocatalytic reaction device according to an eleventh embodiment of the present invention.
Figure 12B:
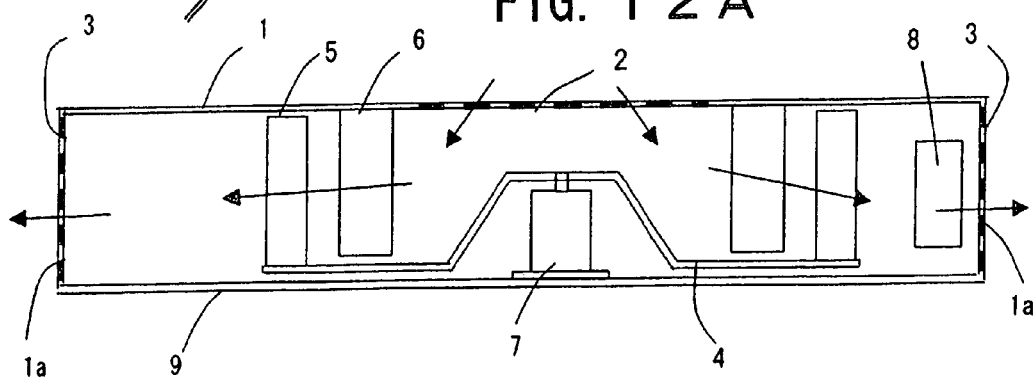

FIG. 12A and FIG. 12B are views showing the construction of a photocatalytic reaction device according to an eleventh embodiment of the present invention.

In the photocatalytic reaction device of this eleventh embodiment, in the photocatalytic reaction device of the tenth embodiment described above, the power source 8 for the motor of the centrifugal type blower 4 is arranged in a corner of the practically square casing 1.

Due to the arrangement of the power source 8 for the motor of the centrifugal type blower 4 in a corner of the practically square casing 1, air flowing out from the discharge ports 3 after flowing out from the series of vanes 5 flows through the vicinity of the power source 8 for the* motor. As a result, cooling of the electronic components that generate heat that are provided in the power source is promoted, increasing reliability.

Twelfth Embodiment

Figure 13A:
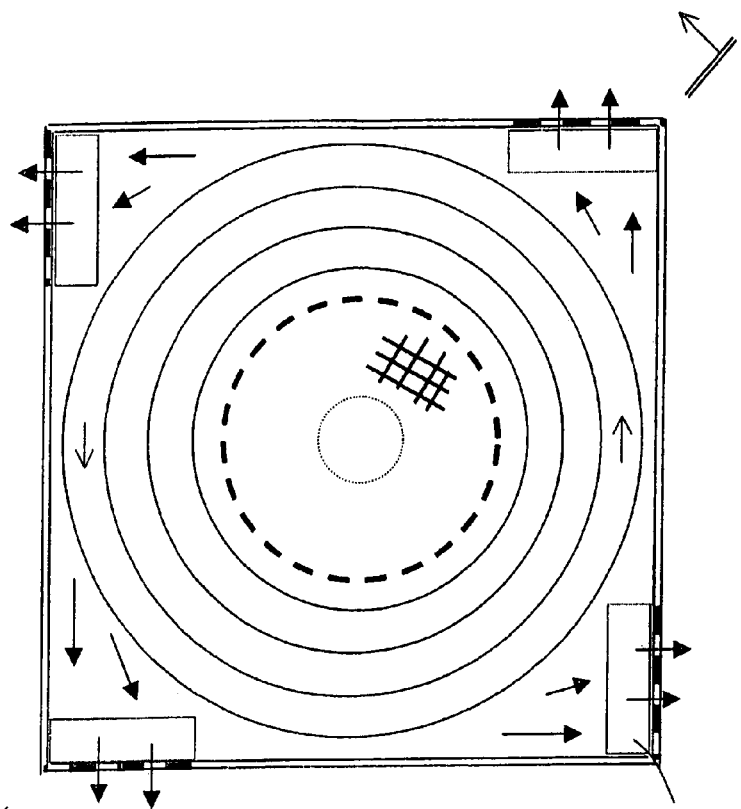
FIG. 13A and FIG. 13B are cross-sectional views showing the construction of a photocatalytic reaction device according to a twelfth embodiment of the present invention.
Figure 13B:
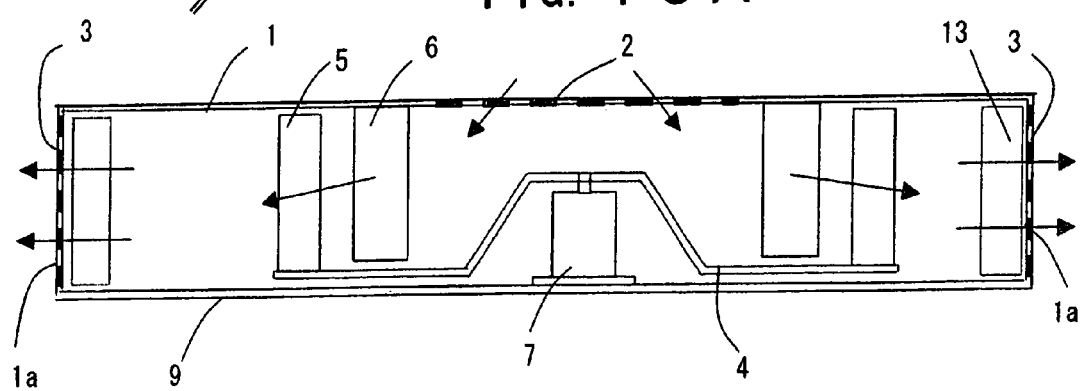

FIG. 13A and FIG. 13B are views showing the construction of a photocatalytic reaction device according to a twelfth embodiment of the present invention.

In the photocatalytic reaction device according to this twelfth embodiment, ozone decomposition filters 13 are arranged in the corners of the practically square casing 1 in the photocatalytic reaction device of the tenth embodiment described above.

Due to this arrangement of the ozone decomposition filters 13 in the corners of a practically square casing 1, of the ozone generated by the ultraviolet rays, any ozone that is not used for decomposition is absorbed by the ozone decomposition filters 13 arranged within the discharge ports 3. Since there is no outflow of excess ozone from the discharge ports 3, sufficient ozone to decompose the impurities in the air can be generated, so that the device according to this embodiment shows a decomposition treatment capability higher than that of the photocatalytic reaction device of the tenth embodiment, described above. Also, although the series of vanes 5 generates fluid noise, noise is attenuated by the arrangement of the photocatalyst carrier 6 at the inner periphery and the ozone decomposition filters 13 within the discharge ports 3, so the noise that is propagated to outside the casing 1 can be reduced.

Thirteenth Embodiment

Figure 14:
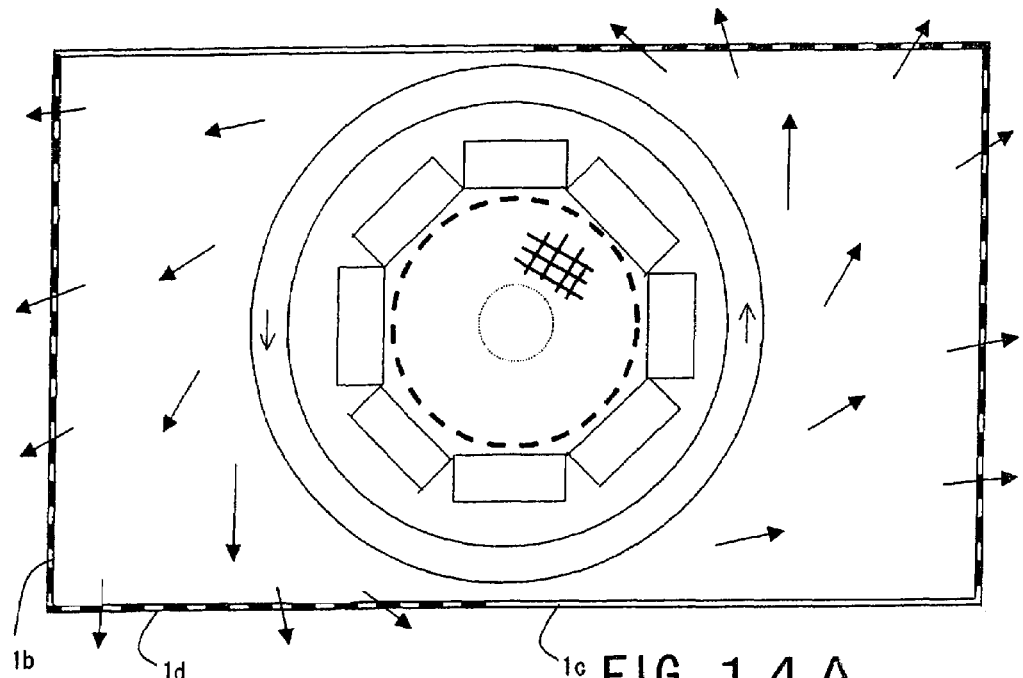
FIG. 14A and FIG. 14B are cross-sectional views showing the construction of a photocatalytic reaction device according to a thirteenth embodiment of the present invention.
Figure 14:
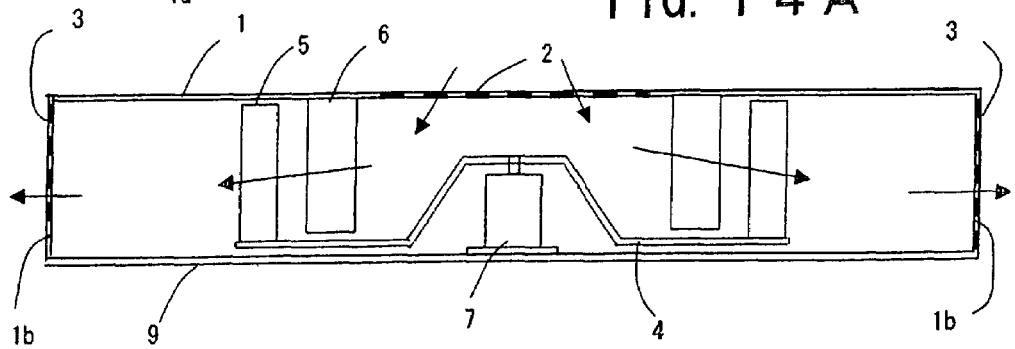

FIG. 14A and FIG. 14B are views showing the construction of a photocatalytic reaction device according to a thirteenth embodiment of the present invention.

Instead of being circular, as in the third embodiment described above, the shape of the casing 1 of the photocatalytic reaction device of this thirteenth embodiment is practically rectangular, when seen in projection from a direction perpendicular to the intake port 2, and discharge ports 3 are arranged in the region of the practically rectangular casing extending from the point of intersection with the side face 1b at the short side, of the side face 1b at the short side and the side face 1c at the long side, up to the point where the distance with respect to the series of vanes 5 of the centrifugal type blower 4 on the downstream side of the fluid is shortest.

In this way, by making the shape of the casing 1 practically rectangular, when seen in projection from a direction perpendicular to the intake port 2, and arranging discharge ports 3 in the region 1d of the practically rectangular casing 1 extending from the point of intersection with the side face 1b at the short side, of the side face 1b at the short side and the side face 1c at the long side, up to the point where the distance with respect to the series of vanes 5 of the centrifugal type blower 4 on the downstream side of the fluid flowing out from the series of vanes 5 of the centrifugal type blower 4 is shortest, the air pressure between the series of vanes 5 and the discharge ports 3 is raised by the air flowing out from the series of vanes 5 but the flow speed becomes smaller due to the wider space than in the case of the tenth embodiment: as a result, the air flows out smoothly from the discharge ports 3. As a result, the flow rate is increased due to the small airflow resistance and a higher decomposition treatment capability in respect of impurities in the air is displayed than in the case of the tenth embodiment.

Fourteenth Embodiment

Figure 15A:
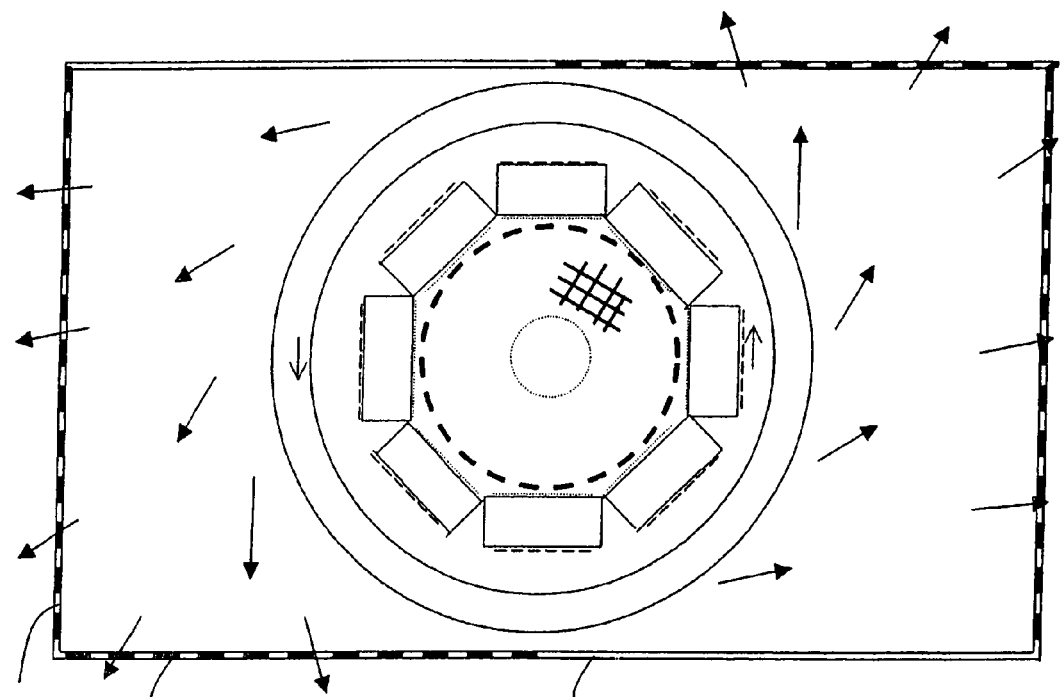
FIG. 15A and FIG. 15B are cross-sectional views showing the construction of a photocatalytic reaction device according to a fourteenth embodiment of the present invention.
Figure 15B:
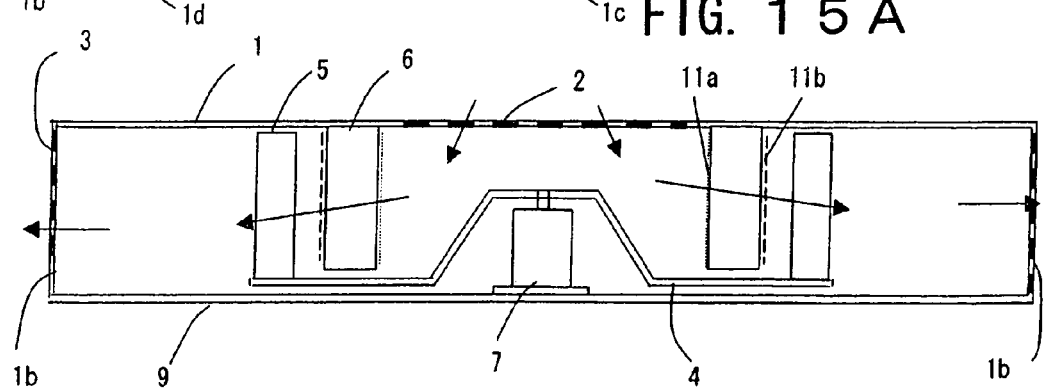

FIG. 15A and FIG. 15B are views showing the construction of a photocatalytic reaction device according to a fourteenth embodiment of the present invention.

In the photocatalytic reaction device according to this fourteenth embodiment, in the photocatalytic reaction device according to the thirteenth embodiment, high-voltage terminals 11a, 11b connected with a high-voltage power source are arranged at the inner periphery and outer periphery of the photocatalyst carrier 6.

Due to the arrangement of the high-voltage terminals 11a, 11b connected with a high-voltage power source at the inner periphery and outer periphery of the photocatalyst carrier 6 in this way, ultraviolet light is generated by causing these to discharge. As a result, the photocatalytic reaction is promoted and a higher decomposition treatment capability in respect of impurities in the air is displayed than in the case of the thirteenth embodiment.

Fifteenth Embodiment

Figure 16A:
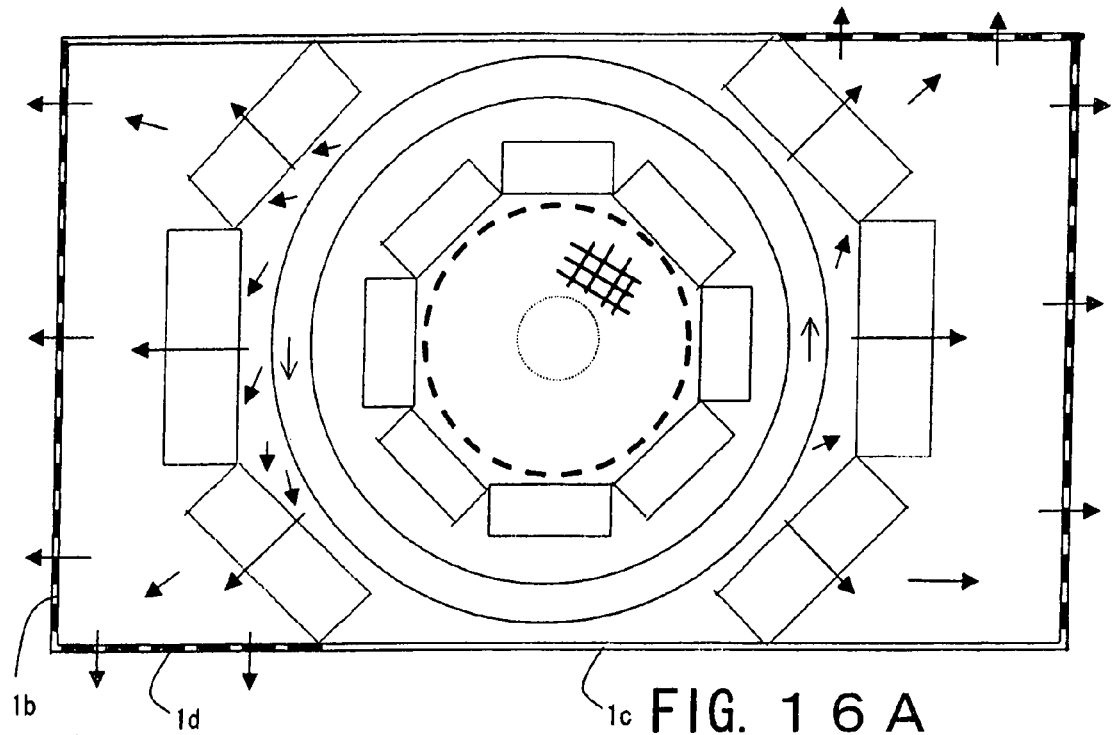
FIG. 16A and FIG. 16B are cross-sectional views showing the construction of a photocatalytic reaction device according to a fifteenth embodiment of the present invention.
Figure 16B:
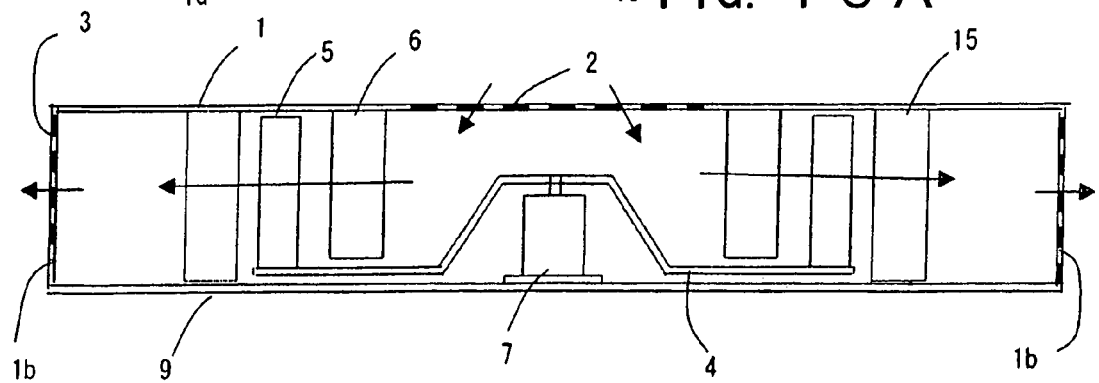

FIG. 16A and FIG. 16B are views showing the construction of a photocatalytic reaction device according to a fifteenth embodiment of the present invention.

In the photocatalytic reaction device of this fifteenth embodiment, in the photocatalytic reaction device of the thirteenth embodiment, deodorizing filters 15 are arranged at the outer periphery of the series of vanes 5 of the centrifugal type blower 4.

By thus arranging deodorizing filters 15 at the outer periphery of the series of vanes 5 of the centrifugal type blower 4, malodorous constituents in the air such as ammonia or hydrogen sulfide can be absorbed and a decomposition treatment capability displayed that is higher than that of the thirteenth embodiment. It should be noted that ozone decomposition filters could also be employed as these deodorizing filters 15. More specifically, many ozone decomposition filters usually have a deodorizing effect of absorbing malodorous constituents such as ammonia or hydrogen sulfide.

Also, although the series of vanes 5 generates fluid noise, since the photocatalyst carrier 6 is arranged at the inner periphery and the deodorizing filters 15 is arranged at the outer periphery, the noise is attenuated and the noise that is propagated to outside the casing 1 can be reduced.

Sixteenth Embodiment

Figure 17A:
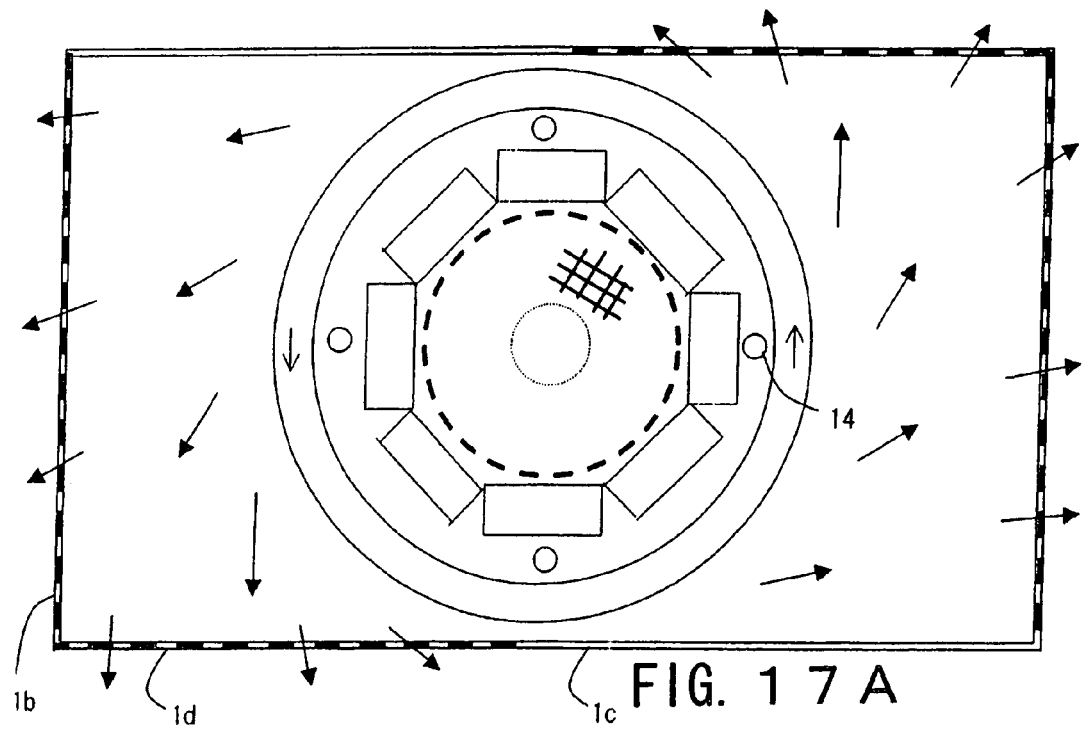
FIG. 17A and FIG. 17B are cross-sectional views showing the construction of a photocatalytic reaction device according to a sixteenth embodiment of the present invention.
Figure 17B:
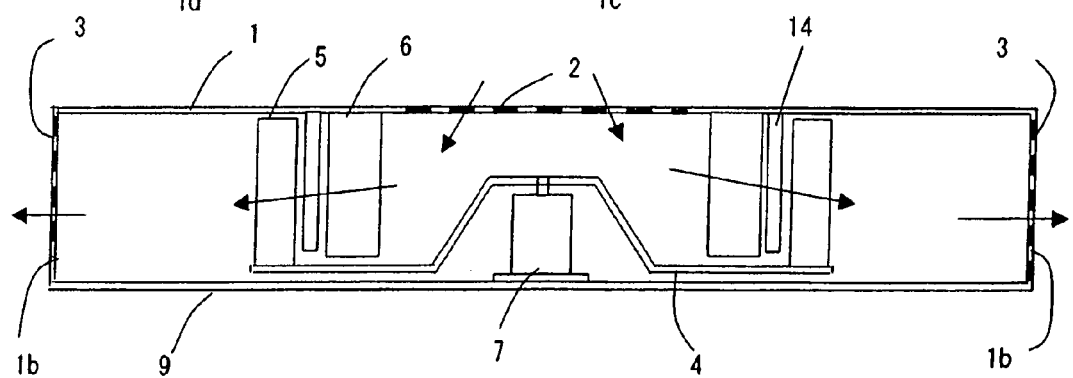

FIG. 17A and FIG. 17B are views showing the construction of a photocatalytic reaction device according to a sixteenth embodiment of the present invention.

In the photocatalytic reaction device of this sixteenth embodiment, in the photocatalytic reaction device of the thirteenth embodiment described above, ultraviolet lamps 14 are arranged at the outer periphery of the photocatalyst carrier 6.

By thus arranging ultraviolet lamps 14 at the outer periphery of the photocatalyst carrier 6, ultraviolet light is directed onto the photocatalyst and, in addition, ultraviolet light reflected by the surface of the series of vanes 5 arranged around the lamps 14 is directed onto the photocatalyst. As a result, the photocatalytic reaction is promoted and a higher decomposition treatment capability in respect of impurities in the air is displayed than in the case of the thirteenth embodiment.

Seventeenth Embodiment

Figure 18A:
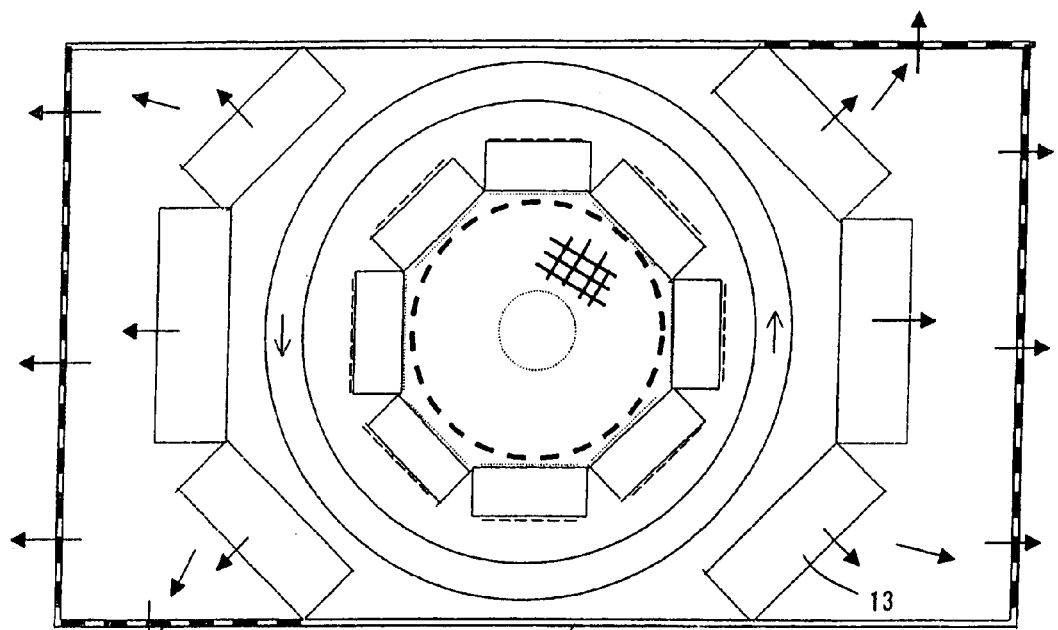
FIG. 18A and FIG. 18B are cross-sectional views showing the construction of a photocatalytic reaction device according to a seventeenth embodiment of the present invention.
Figure 18B:
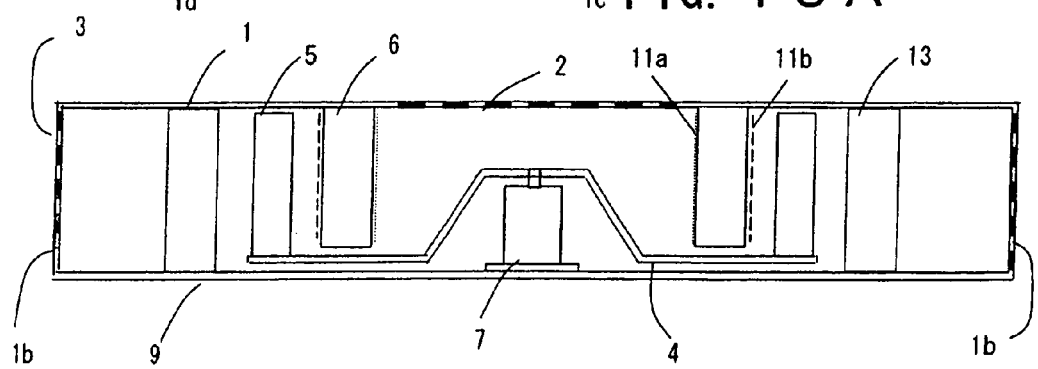

FIG. 18A and FIG. 18B are views showing the construction of a photocatalytic reaction device according to a seventeenth embodiment of the present invention.

In the photocatalytic reaction device of this seventeenth embodiment, in the photocatalytic reaction device of the fourteenth embodiment described above, ozone decomposition filters 13 are arranged at the outer periphery of the series of vanes 5 of the centrifugal type blower 4.

By thus arranging ozone decomposition filters 13 at the outer periphery of the series of vanes 5 of the centrifugal type blower 4, any ozone generated by the ultraviolet rays that is not used for decomposition is absorbed by the ozone decomposition filters 13 arranged on the inside of the discharge ports 3. Since there is no outflow of excess ozone from the discharge ports 3, sufficient ozone to decompose impurities in the air can be generated and a high decomposition treatment capability as in the fourteenth embodiment is displayed. Also, although the series of vanes 5 generates fluid noise, since the photocatalyst carrier 6 is arranged at the inner periphery and the ozone decomposition filters 13 are arranged at the outer periphery, the noise is attenuated and the noise that is propagated to outside the casing 1 can be reduced.

Eighteenth Embodiment

Figure 19A:
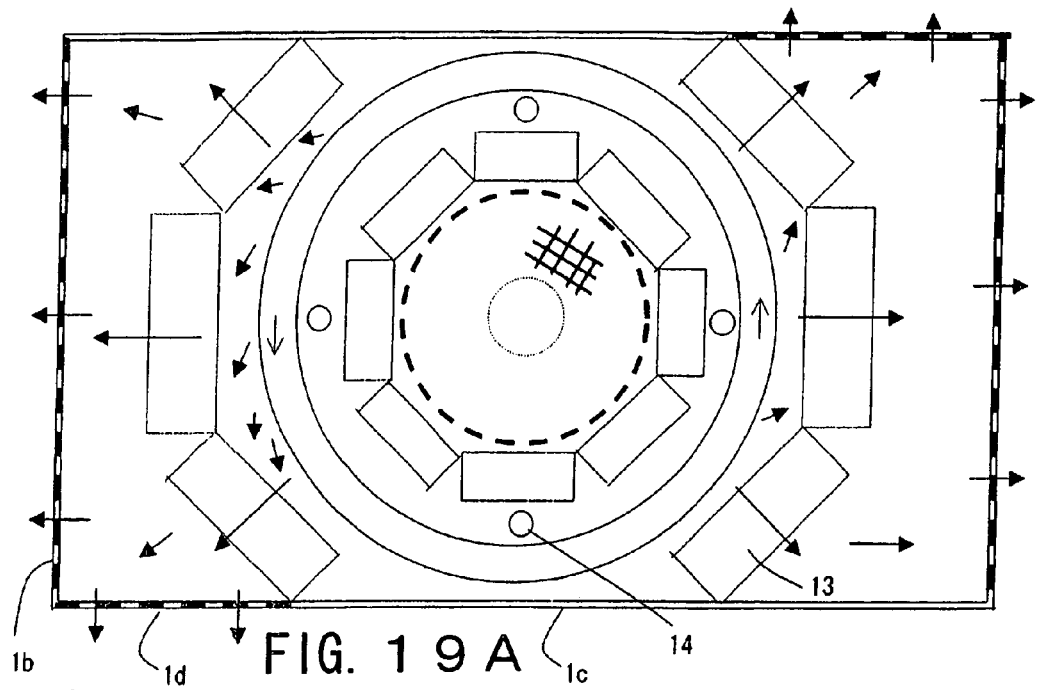
FIG. 19A and FIG. 19B are cross-sectional views showing the construction of a photocatalytic reaction device according to an eighteenth embodiment of the present invention.
Figure 19B:
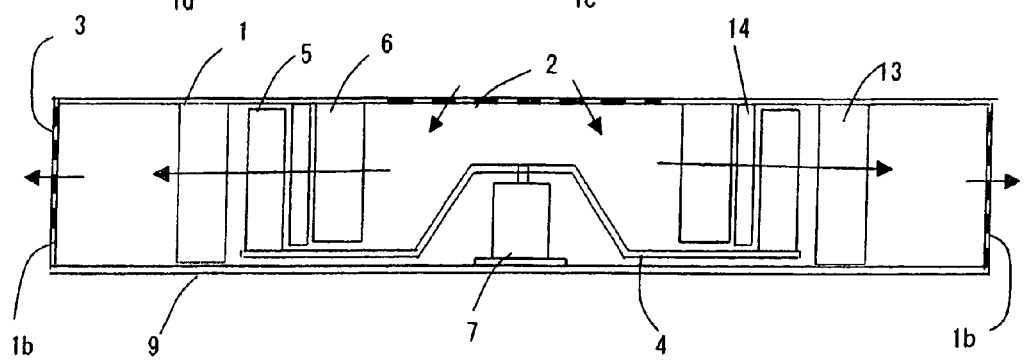

FIG. 19A and FIG. 19B are views showing the construction of a photocatalytic reaction device according to an eighteenth embodiment of the present invention.

In a photocatalytic reaction device according to this eighteenth embodiment, in the photocatalytic reaction device of the sixteenth embodiment described above, ozone decomposition filters 13 are arranged at the outer periphery of the series of vanes 5 of the centrifugal type blower 4.

By thus arranging ozone decomposition filters 13 at the outer periphery of the series of vanes 5 of the centrifugal type blower 4, any ozone generated by the ultraviolet rays that was not used for decomposition is absorbed by the ozone decomposition filters 13 arranged on the inside of the discharge ports 3. Since there is no outflow of excess ozone from the discharge ports 3, sufficient ozone to decompose impurities in the air can be generated and a high decomposition treatment capability as in the sixteenth embodiment is displayed. Also, although the series of vanes 5 generates fluid noise, since the photocatalyst carrier 6 is arranged at the inner periphery and the ozone decomposition filters 13 are arranged at the outer periphery, the noise is attenuated and the noise that is propagated to outside the casing 1 can be reduced.

Nineteenth Embodiment

FIG. 20A and FIG. 20B are views showing the construction of a photocatalytic reaction device according to a nineteenth embodiment of the present invention.

In the photocatalytic reaction device of this nineteenth embodiment, the projection of the casing from a direction perpendicular with respect to the intake port 2 formed in the casing 1 is made practically rectangular, discharge ports 3 are provided at a plurality of locations on a side face of the casing different from that of the intake port 2 (for example, prescribed locations on the short side face 1b and the long side face 1c), the series of vanes 5 of the centrifugal type blower 4 is arranged around the intake port 2 within the casing, a photocatalyst carrier 6 that carries a visible light reaction type photocatalyst is arranged at the outer periphery of the series of vanes 5 of the centrifugal type blower 4, deodorizing filters 15 are arranged on the discharge port 3 side of the photocatalyst carrier 6, the discharge ports 3 are arranged facing the outlet site of the deodorizing filters 15, and portions 1e of the upper face and lower face of the casing 1 facing the photocatalyst carrier 6 are made transparent. It should be noted that it would also be possible to make the portion 1e facing the photocatalyst carrier 6 of only one of the upper face and lower face of the casing 1 transparent.

By thus making at least part of the portions of the casing 1 facing the photocatalyst carrier 6 transparent, a considerable amount of visible light strikes the photocatalyst carrier 6, promoting the photocatalytic reaction and a high decomposition treatment capability in respect of impurities in the air is displayed.

Also, since the discharge ports 3 are provided in a plurality of locations, the area of the flow paths to the discharge ports 3 is increased in comparison with the prior art case, where a discharge port 3 was provided at a single location only, and higher decomposition treatment capability in respect of impurities in the air is displayed compared with conventionally.

Twentieth Embodiment

FIG. 21A and FIG. 21B are views showing the construction of a photocatalytic reaction device according to a twentieth embodiment of the present invention.

In the photocatalytic reaction device of this twentieth embodiment, the projection of the casing from a direction perpendicular with respect to the intake port 2 formed in the casing 1 is made practically rectangular, discharge ports 3 are provided at a plurality of locations on a side face of the casing different from that of the intake port 2, for example, prescribed locations on the short side face 1b and the long side face 1c, the series of vanes 5 of the centrifugal type blower 4 is arranged around the intake port 2 within the casing, a photocatalyst carrier 6 that carries a photocatalyst is arranged at the outer periphery of the series of vanes 5 of the centrifugal type blower 4, ozone decomposition filters 13 are arranged on the discharge port side of the photocatalyst carrier, the discharge ports 3 are arranged facing the outlet site of the ozone decomposition filters 13, and high-voltage terminals 11a, 11b connected with a high-voltage power source are arranged on the intake port side and the discharge port side of the photocatalyst carrier 6.

By thus arranging high-voltage terminals 11a, 11b connected with a high-voltage power source on the intake port side and the discharge port side of the photocatalyst carrier 6, ultraviolet light is generated by causing these to discharge. As a result, the photocatalytic reaction is promoted and a higher decomposition treatment capability in respect of impurities in the air is displayed.

Also, by making the photocatalyst carried by the photocatalyst carrier 6 a visible light reaction type photocatalyst, and making at least part of the portions of the casing 1 facing the photocatalyst carrier 6 transparent, a considerable amount of visible light strikes the photocatalyst carrier 6, promoting the photocatalytic reaction and a high decomposition treatment capability in respect of impurities in the air is displayed.

Also, since the discharge ports 3 are provided in a plurality of locations, the area of the flow paths to the discharge ports 3 is increased in comparison with the prior art case, where a discharge port 3 was provided at a single location only, and higher decomposition treatment capability in respect of impurities in the air is displayed compared with conventionally.

Twenty-First Embodiment

Figures 22A, 22B:
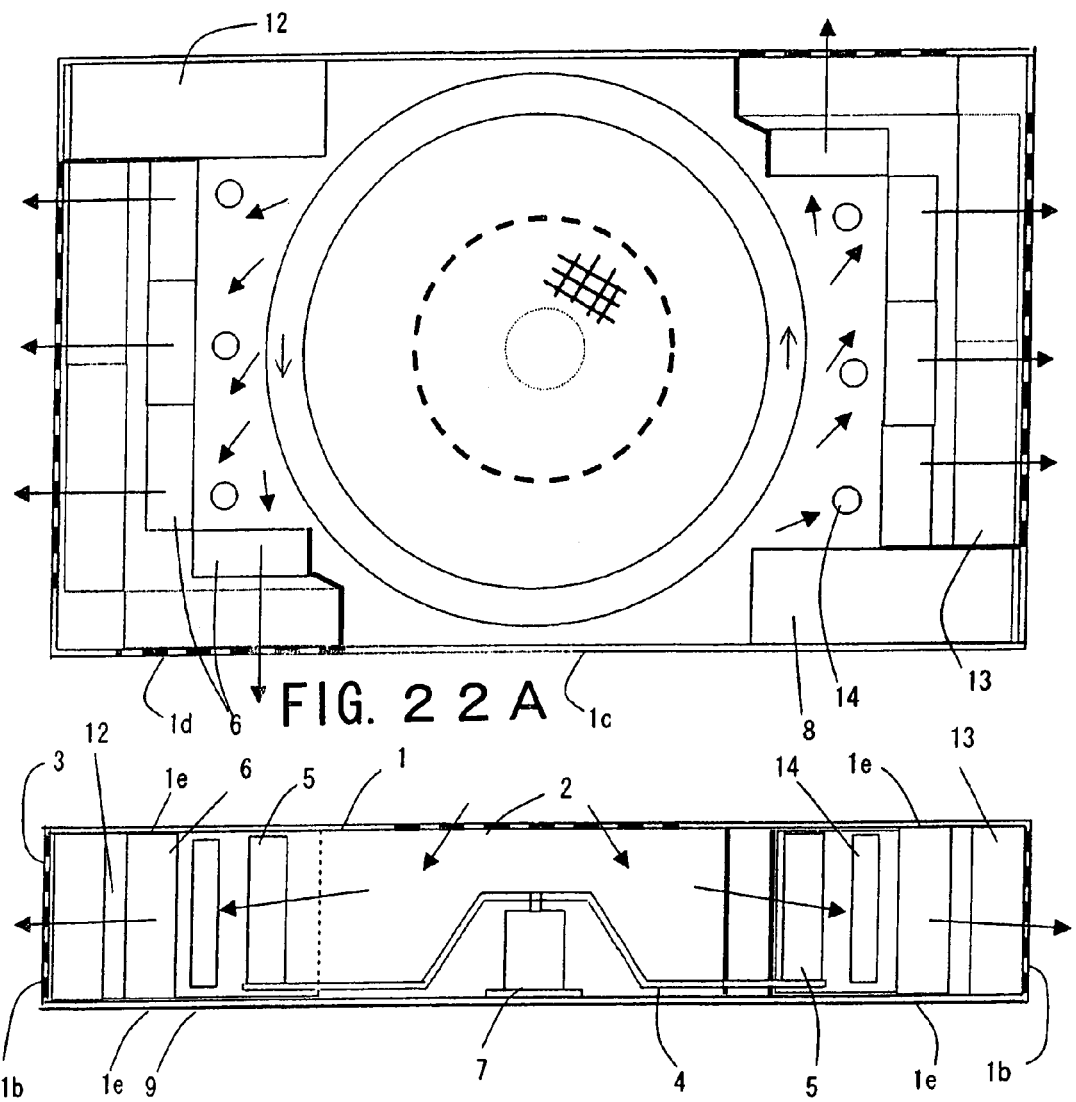
FIG. 22A and FIG. 22B are cross-sectional views showing the construction of a photocatalytic reaction device according to a twenty-first embodiment of the present invention.

FIG. 22A and FIG. 22B are views showing the construction of a photocatalytic reaction device according to a twenty-first embodiment of the present invention.

In the photocatalytic reaction device of this twenty-first embodiment, the projection of the casing from a direction perpendicular with respect to the intake port 2 formed in the casing 1 is made practically rectangular, discharge ports 3 are provided at a plurality of locations on a side face of the casing different from that of the intake port 2, for example, prescribed locations on the short side face 1b and the long side face 1c, the series of vanes 5 of the centrifugal type blower 4 is arranged around the intake port 2 within the casing, a photocatalyst carrier 6 that carries a photocatalyst is arranged at the outer periphery of the series of vanes 5 of the centrifugal type blower 4, ozone decomposition filters 13 are arranged on the discharge port side of the photocatalyst carrier, the discharge ports 3 are arranged facing the outlet site of the ozone decomposition filters 13, and ultraviolet lamps 14 are arranged at the outer periphery of the series of vanes 5 of the centrifugal type blower 4.

By thus arranging ultraviolet lamps 14 at the outer periphery of the series of vanes 5 of the centrifugal type blower 4, ultraviolet light is directed onto the photocatalyst carried by the photocatalyst carrier 6 and, in addition, ultraviolet light reflected at the surface of the series of vanes 5 arranged around the lamps 14 is directed onto the photocatalyst carrier by the photocatalyst carrier 6. As a result, the photocatalytic reaction is promoted and a higher decomposition treatment capability in respect of impurities in the air is displayed.

Also, by making the photocatalyst carried by the photocatalyst carrier 6 a visible light reaction type photocatalyst, and making at least part of the portions of the casing 1 facing the photocatalyst carrier 6 transparent, a considerable amount of visible light strikes the photocatalyst carrier 6, promoting the photocatalytic reaction and a high decomposition treatment capability in respect of impurities in the air is displayed.

Also, since the discharge ports 3 are provided in a plurality of locations, the area of the flow paths to the discharge ports 3 is increased in comparison with the prior art case, where a discharge port 3 was provided at a single location only, and higher decomposition treatment capability in respect of impurities in the air is displayed compared with conventionally.

Twenty-Second Embodiment

Figure 23A:
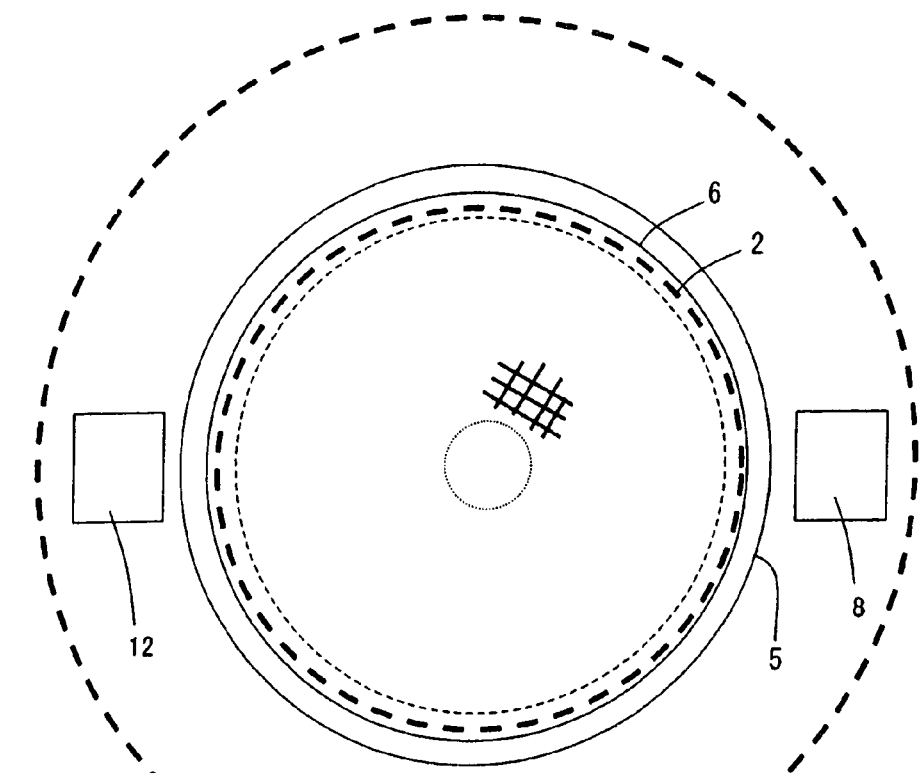
FIG. 23A and FIG. 23B are cross-sectional views showing the construction of a photocatalytic reaction device according to a twenty-second embodiment of the present invention.
Figure 23B:
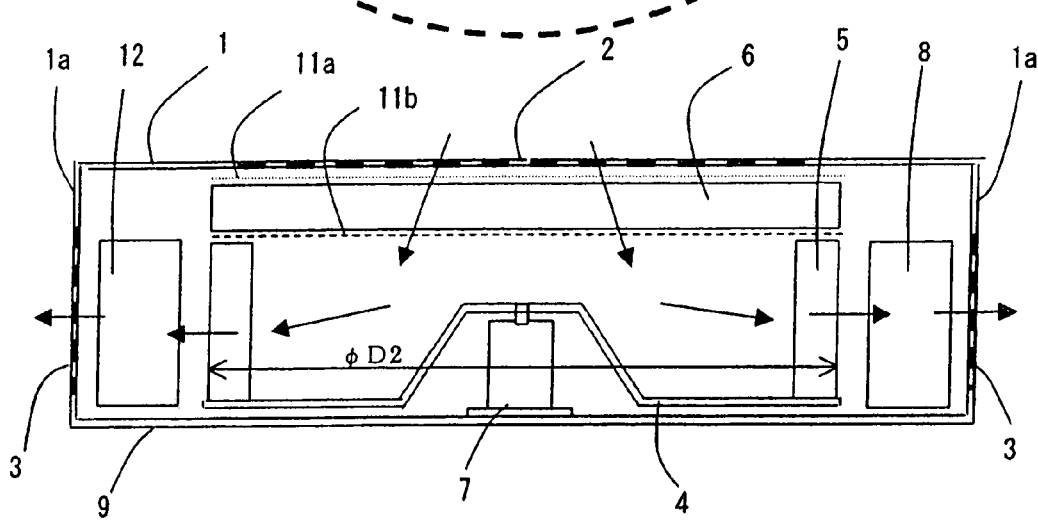

FIG. 23A and FIG. 23B are views showing the construction of a photocatalytic reaction device according to a twenty-second embodiment of the present invention.

In the embodiments described above, the photocatalyst carrier 6 provided between the intake port 2 and discharge ports 3 was provided at the inner periphery or outer periphery of the series of vanes 5 of the centrifugal type blower 4 around the intake port 2, but, in this twenty-second embodiment, the photocatalyst carrier 6 is provided facing the intake port 2.

Specifically, in the photocatalytic reaction device 9 of this embodiment, an intake port 2 is formed having apertures in the form of a mesh, in the middle of the upper face of a cylindrical casing 1. Also, a plurality of discharge ports 3 having apertures formed in the form of a mesh are formed in a side face of the casing 1 different from that of this intake port 2.

The series of vanes 5 of the centrifugal type blower 4 for feeding air flowing in from the intake port 2 to the discharge ports 3 are arranged around the intake port 2 within the casing 1 and a photocatalyst carrier 6 that carries the photocatalyst and is made of a porous body and is for example shaped as a circular plate is arranged on the side of the series of vanes 5 of this centrifugal type blower 4 facing the intake port 2. That is, the photocatalyst carrier 6 is arranged facing the intake port 2 and the series of vanes 5 of the centrifugal type blower 4 is arranged facing the opposite side of this photocatalyst carrier 6 to that of the intake port.

Also, high-voltage terminals 11a, 11b that are connected with a high-voltage power source 12 are arranged on both sides of the photocatalyst carrier 6 i.e. at the photocatalyst carrier 6 on the upstream side and downstream side of the inflowing air. A construction is adopted in which discharge ports 3 are arranged on a side face of the casing 1 of the photocatalytic reaction device 9, at least two discharge ports being arranged in directions differing by practically 180° in the radial direction of the series of vanes 5 of the centrifugal type blower 4, or a plurality of discharge ports being arranged around the centrifugal type blower 4, or the discharge ports being arranged in continuous fashion along the entire circumferential surface of the side face of the casing 1.

In the construction of this embodiment, the partition 20 that was conventionally present in the vicinity of the series of vanes 5 is absent, so the fan characteristic is shifted from C0 to C1 i.e. towards larger flow rate and larger static pressure. Also, the airflow resistance is reduced by the increase of area of the flow paths to the discharge ports 3, being reduced from R0 to R1. As a result, the operating flow rate is increased from the conventional value of Q0 to Q1 and a higher decomposition treatment capability in respect of impurities in the air than conventionally is displayed. Also, ultraviolet light is generated by discharge between the high-voltage terminals 11a and 11b, promoting the decomposition action of the photocatalyst. The ozone that is then generated by the ultraviolet light performs oxidative decomposition of impurities in the air.

Twenty-Third Embodiment

Figure 24A:
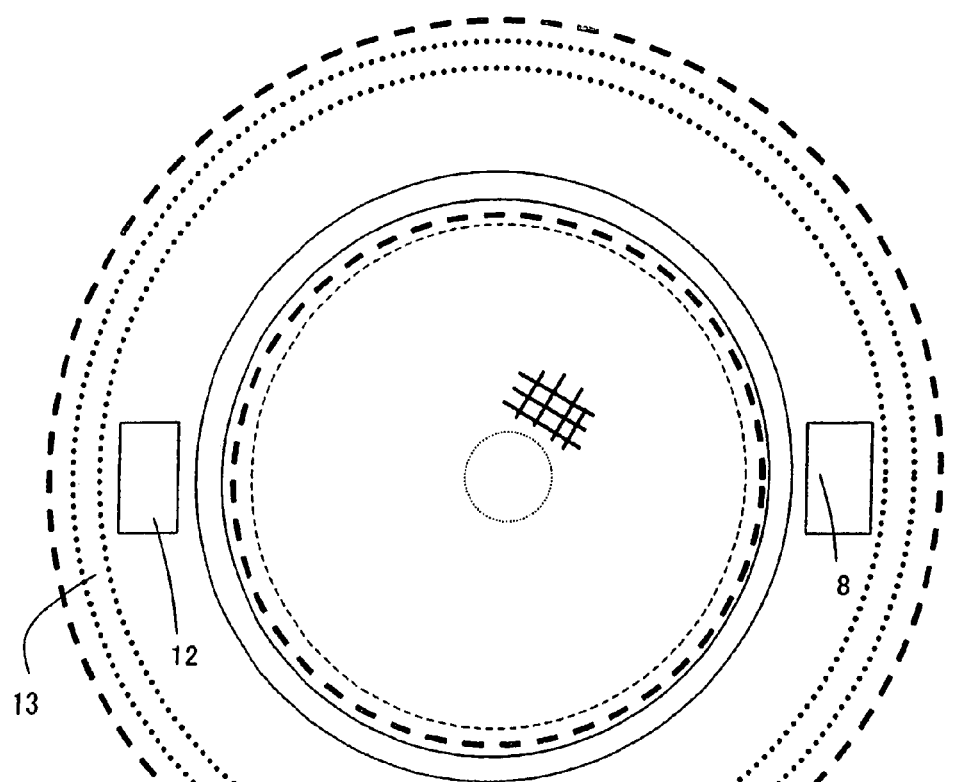
FIG. 24A and FIG. 24B are cross-sectional views showing the construction of a photocatalytic reaction device according to a twenty-third embodiment of the present invention.
Figure 24B:
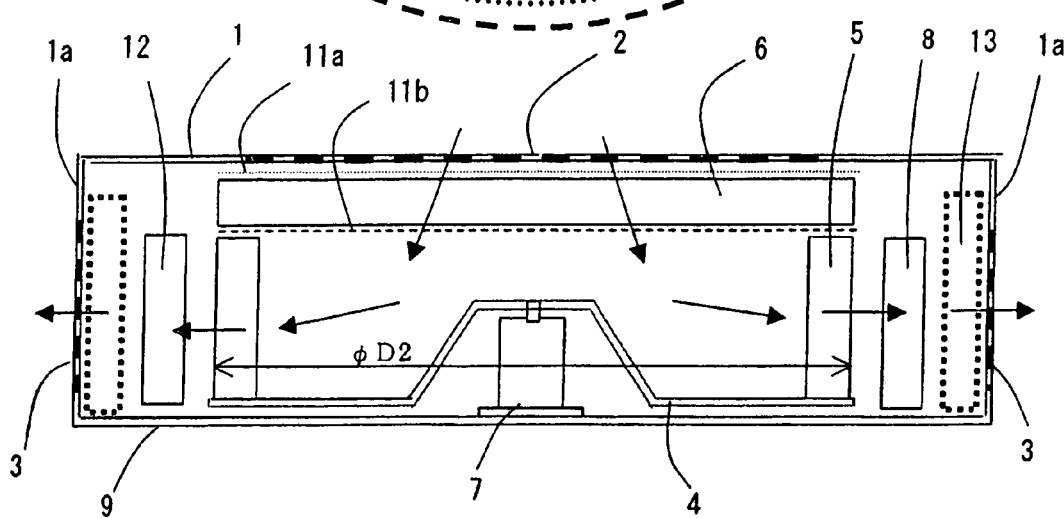

FIG. 24A and FIG. 24B are views showing the construction of a photocatalytic reaction device according to a twenty-third embodiment of the present invention.

A photocatalytic reaction device according to this twenty-third embodiment has a construction in which ozone decomposition filters 13 are arranged on the inside of these discharge ports 3 in the twenty-second embodiment described above.

The decomposition action of the photocatalyst is promoted by generation of ultraviolet light by discharge between the high-voltage terminals 11a and 11b. The ozone that is then generated by the ultraviolet light performs oxidative decomposition of impurities in the air. Ozone that was not used in the decomposition is absorbed by the ozone decomposition filters 13. As a result, since there is no outflow of excess ozone from the discharge ports 3, sufficient ozone to decompose the impurities in the air can be generated, so that a decomposition treatment capability higher than that of the photocatalytic reaction device of the twenty-second embodiment, described above is displayed.

Also, although the series of vanes 5 generates fluid noise, noise is attenuated by the arrangement of the photocatalyst carrier 6 and the side of the intake port 2 and the ozone decomposition filters 13 at the side of the discharge ports 3, so the noise that is propagated to outside the casing 1 can be reduced.

Twenty-Fourth Embodiment

Figure 25A:
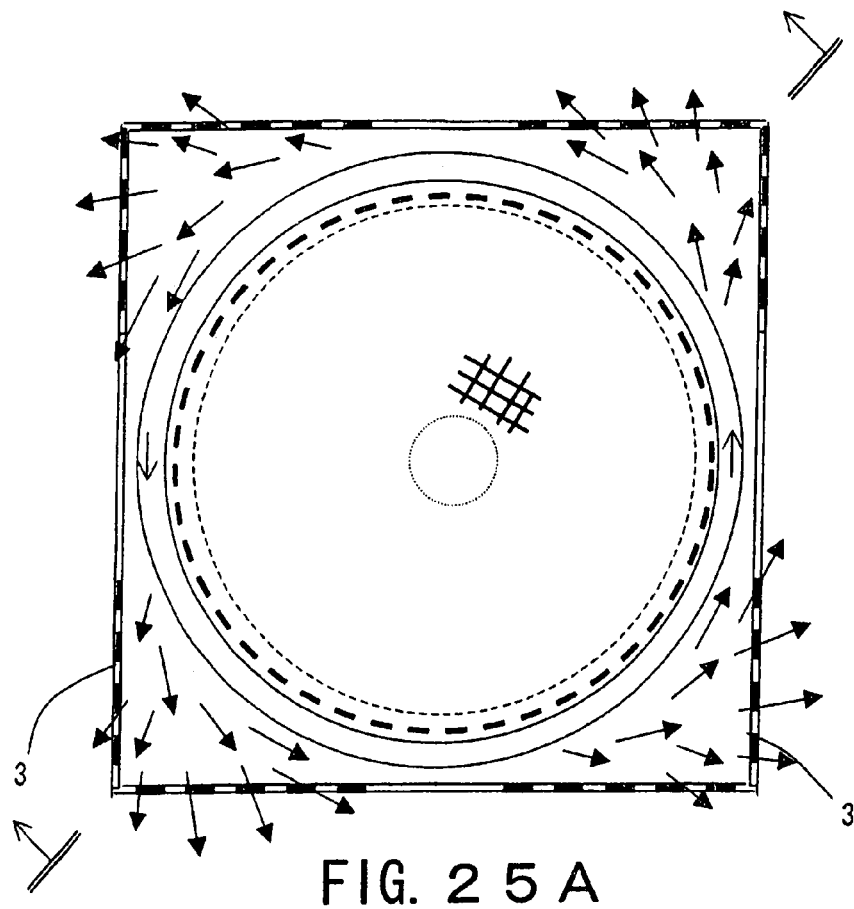
FIG. 25A and FIG. 25B are cross-sectional views showing the construction of a photocatalytic reaction device according to a twenty-fourth embodiment of the present invention.
Figure 25B:
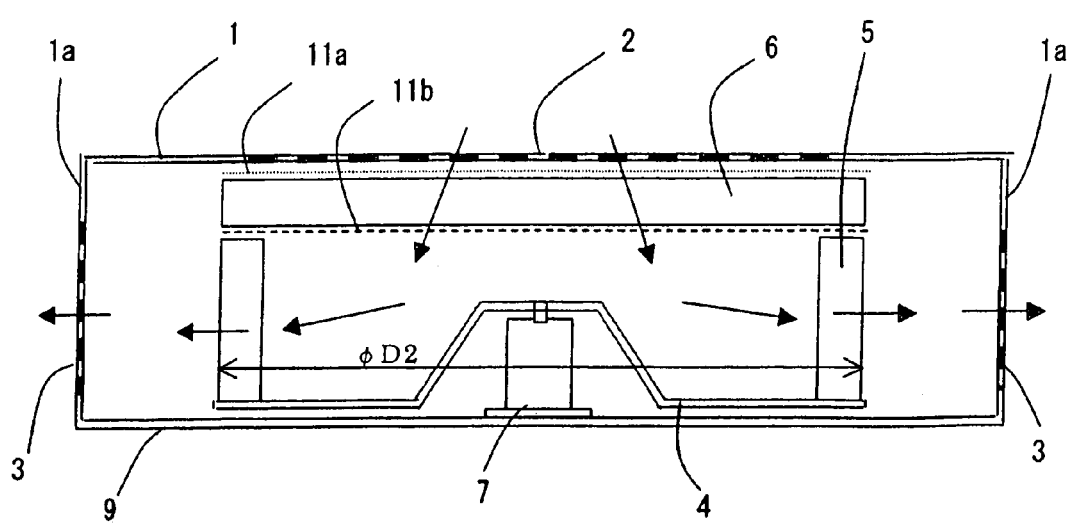

FIG. 25A and FIG. 25B are views showing the construction of a photocatalytic reaction device according to a twenty-fourth embodiment of the present invention.

In these Figures, the lower Figure is a view showing a cross-section viewed in the direction of the arrows at the position of a diagonal of a practically square casing 1 in the upper Figure.

In the photocatalytic reaction device of this twenty-fourth embodiment, in a projection of the shape of the casing from a direction perpendicular to the intake port, the shape of the casing is practically square instead of being circular as in the case of the twenty-second embodiment described above, and the discharge ports 3 are arranged at the corners of this practically square casing.

By making the casing 1 practically square in projection from the direction perpendicular to the intake port 2 and arranging the discharge ports 3 at the corners of this practically square casing 1, the air pressure at the corners is increased by the air flowing out from the series of vanes 5, so that the air flows out smoothly from the discharge ports 3. As a result, in spite of the practically square shape of the casing 1 of smaller area in projection in the axial direction of the casing 1 compared with the twenty-second embodiment, due to the smaller airflow resistance, the flow rate is practically unchanged and the device therefore shows a decomposition treatment capability in respect of impurities in the air that is on the same level with that of the twenty-second embodiment.

Twenty-Fifth Embodiment

Figure 26A:
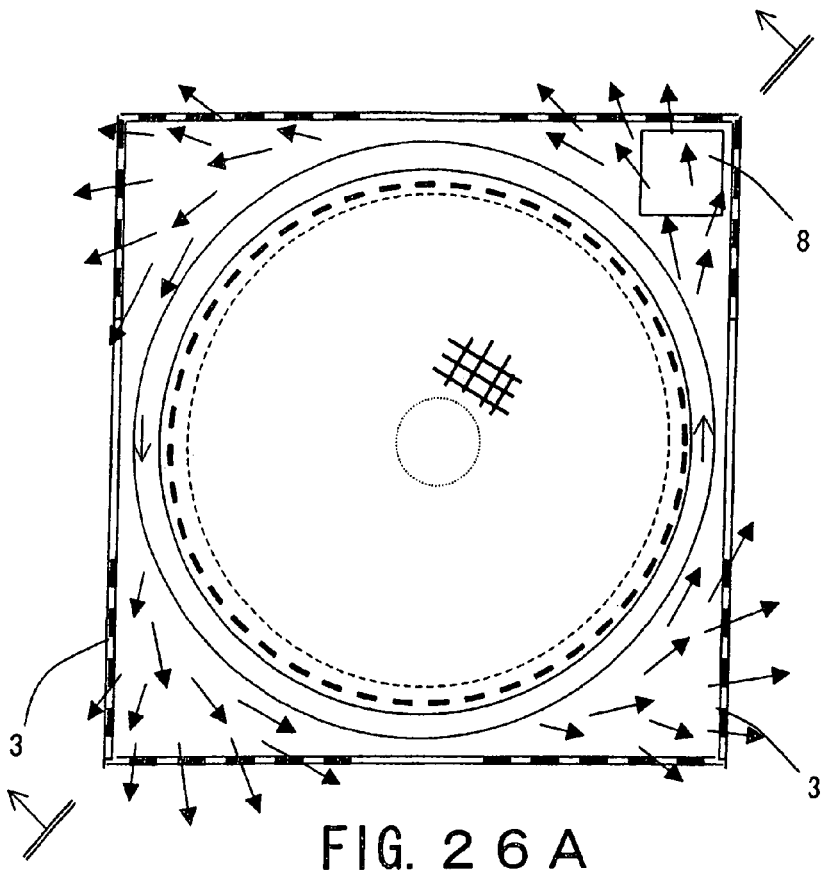
FIG. 26A and FIG. 26B are cross-sectional views showing the construction of a photocatalytic reaction device according to a twenty-fifth embodiment of the present invention.
Figure 26B:
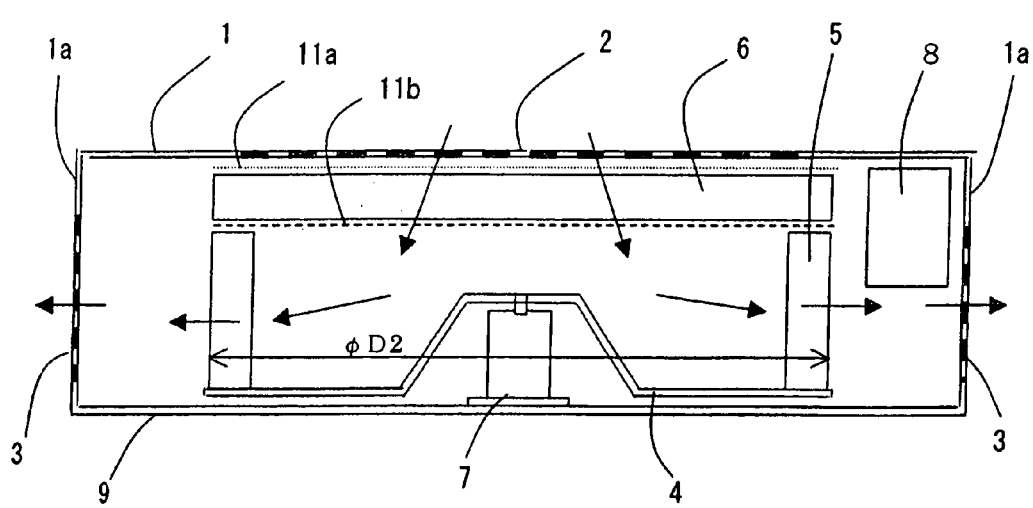

FIG. 26A and FIG. 26B are views showing the construction of a photocatalytic reaction device according to a twenty-fifth embodiment of the present invention.

In the photocatalytic reaction device of this twenty-fifth embodiment, in the photocatalytic reaction device of the twenty-fourth embodiment described above, the power source 8 for the motor of the centrifugal type blower 4 is arranged at a corner of the practically square casing 1.

By arranging the power source 8 for the motor of the centrifugal type blower 4 at a corner of the practically square casing 1, the air flowing out from the discharge ports 3 after flowing out from the series of vanes 5 flows through the vicinity of the power source 8 for the motor. As a result, cooling of the electronic components that generate heat that are provided in the power source is promoted, increasing reliability.

Twenty-Sixth Embodiment

Figure 27A:
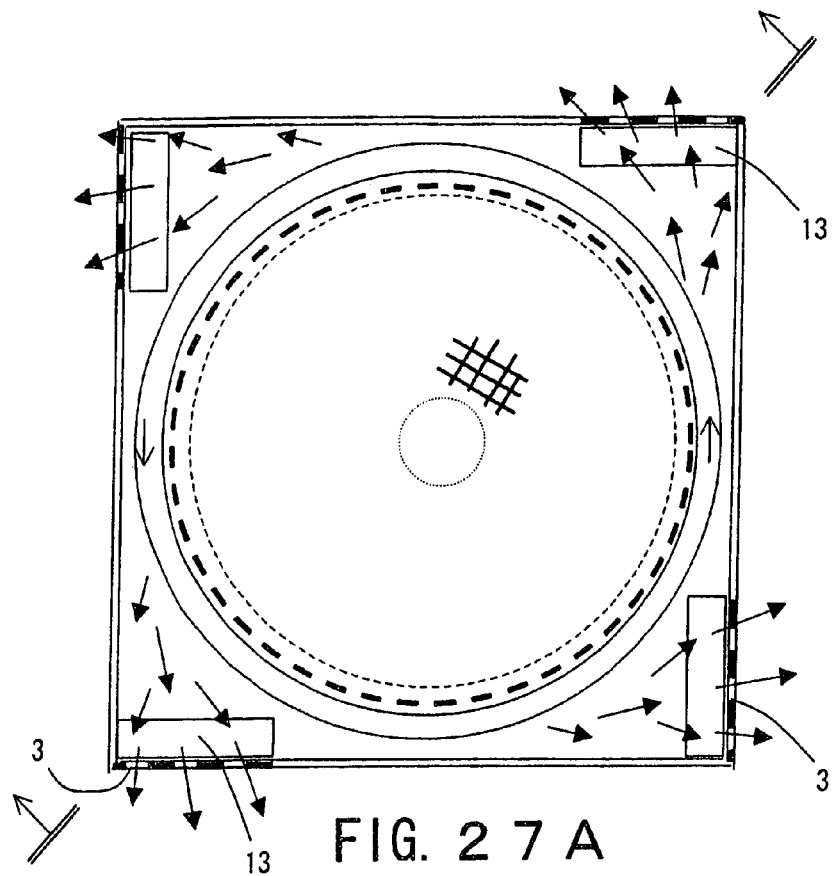
FIG. 27A and FIG. 27B are cross-sectional views showing the construction of a photocatalytic reaction device according to a twenty-sixth embodiment of the present invention.
Figure 27B:
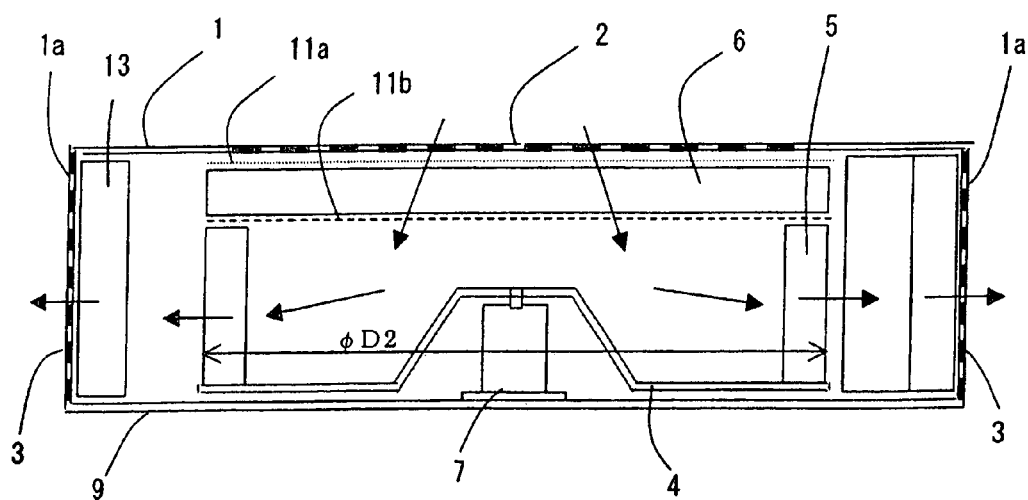

FIG. 27A and FIG. 27B are views showing the construction of a photocatalytic reaction device according to a twenty-sixth embodiment of the present invention.

In the photocatalytic reaction device of this twenty-sixth embodiment, in the photocatalytic reaction device of the twenty-fifth embodiment described above, ozone decomposition filters 13 are arranged at the corners of the practically square casing 1.

By arranging ozone decomposition filters 13 at the corners of the practically square casing 1, any ozone generated by the ultraviolet rays that is not used in decomposition is absorbed by the ozone decomposition filters 13 arranged on the inside of the discharge ports 3. Since no excess ozone flows out from the ozone discharge ports 3, sufficient ozone can be generated to decompose the impurities in the air and a higher decomposition treatment capability is displayed than that of the twenty-fifth embodiment. Also, although fluid noise is generated by the series of vanes 5, since the photocatalyst carrier 6 is arranged on the side of the intake port 2 and the ozone filters 13 are arranged on the side of the discharge ports 3, the noise is attenuated and the noise propagated to outside of the casing 1 can be reduced.

Twenty-Seventh Embodiment

Figure 28A:
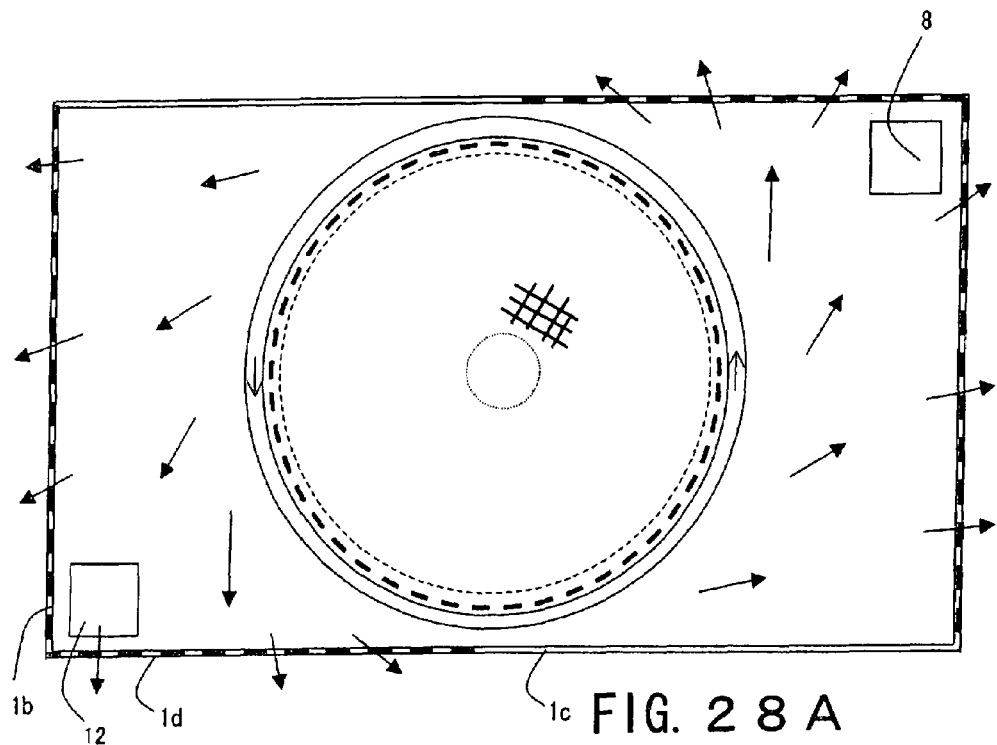
FIG. 28A and FIG. 28B are cross-sectional views showing the construction of a photocatalytic reaction device according to a twenty-seventh embodiment of the present invention.
Figure 28B:
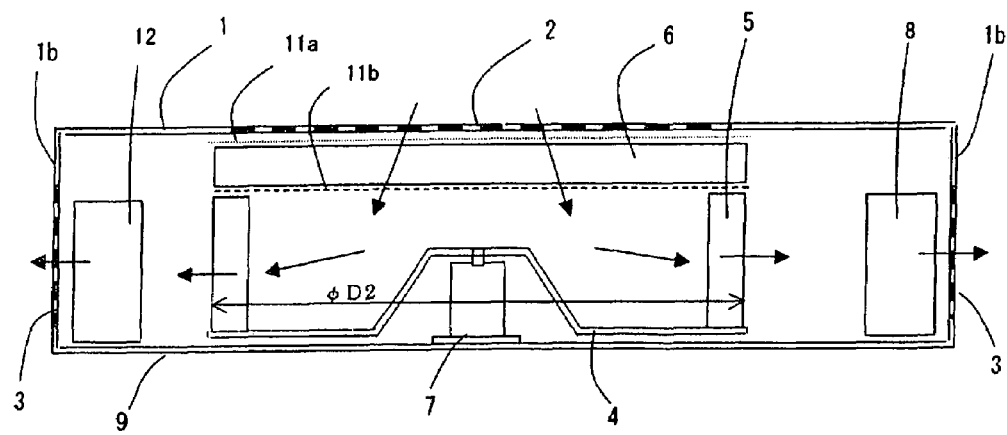

FIG. 28A and FIG. 28B are views showing the construction of a photocatalytic reaction device according to a twenty-seventh embodiment of the present invention.

Instead of being practically square, as in the twenty-fourth embodiment described above, the shape of the casing 1 of the photocatalytic reaction device of this twenty-seventh embodiment is practically rectangular, when seen in projection from a direction perpendicular to the intake port 2, and the discharge ports 3 are arranged in the region of the practically rectangular casing extending from the point of intersection with the side face 1b at the short side, of the side face 1b at the short side and the side face 1c at the long side, up to the point where the distance with respect to the series of vanes 5 of the centrifugal type blower 4 on the downstream side of the fluid is shortest.

Thus by making the casing 1 of the photocatalytic reaction device practically rectangular in this way, when seen in projection from a direction perpendicular to the intake port 2, and arranging the discharge ports 3 in the region 1d of the practically rectangular casing 1 extending from the point of intersection with the side face 1b at the short side, of the side face 1b at the short side and the side face 1c at the long side, up to the point where the distance with respect to the series of vanes 5 of the centrifugal type blower 4 on the downstream side of the fluid is shortest, the air pressure between the series of vanes 5 and the discharge ports 3 is raised by the air flowing out from the series of vanes 5 but the flow speed becomes smaller due to the wider space than in the case of the twenty-fourth embodiment: as a result, the air flows out smoothly from the discharge ports 3. As a result, the flow rate is increased due to the small airflow resistance and a higher decomposition treatment capability in respect of impurities in the air is displayed than in the case of the twenty-fourth embodiment.

Twenty-Eighth Embodiment

Figure 29A:
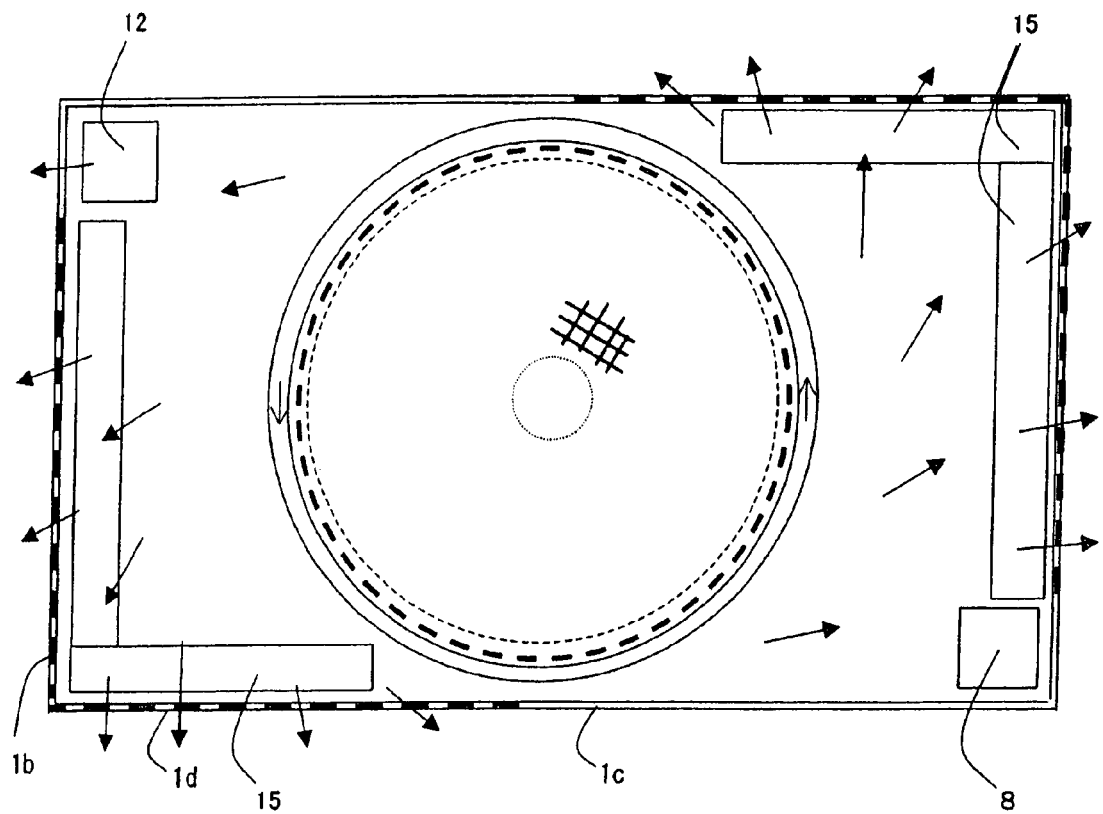
FIG. 29A and FIG. 29B are cross-sectional views showing the construction of a photocatalytic reaction device according to a twenty-eighth embodiment of the present invention.
Figure 29B:
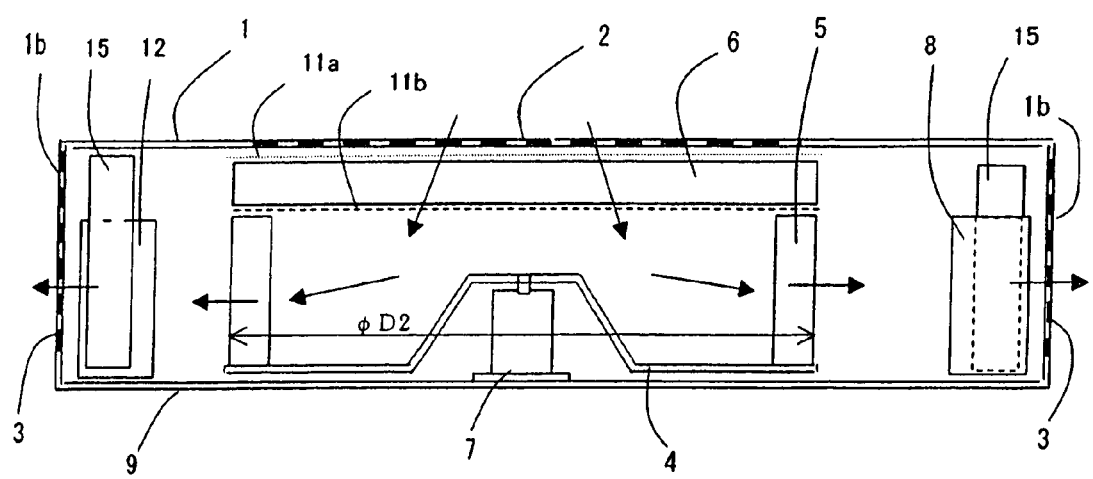

FIG. 29A and FIG. 29B are views showing the construction of a photocatalytic reaction device according to a twenty-eighth embodiment of the present invention.

In the photocatalytic reaction device of this twenty-eighth embodiment, in the photocatalytic reaction device of the twenty-seventh embodiment, deodorizing filters 15 are arranged at the outer periphery of the series of vanes 5 of the centrifugal type blower 4.

By thus arranging deodorizing filters 15 for example in the vicinity of a discharge ports 3 at the outer periphery of the series of vanes 5 of the centrifugal type blower 4, malodorous constituents such as ammonia or hydrogen sulfide in the air can be absorbed and a higher decomposition treatment capability than in the case of the twenty-seventh embodiment is displayed. It should be noted that ozone decomposition filters could be employed as these deodorizing filters 15. More specifically, many ozone decomposition filters usually have a deodorizing effect of absorbing malodorous constituents such as ammonia or hydrogen sulfide.

Also, although the series of vanes 5 generates fluid noise, noise is attenuated by the arrangement of the photocatalyst carrier 6 at the side of the intake port 2 and the deodorizing filters 15 at the outer periphery thereof, so the noise that is propagated to outside the casing 1 can be reduced.

Twenty-Ninth Embodiment

Figure 30A:
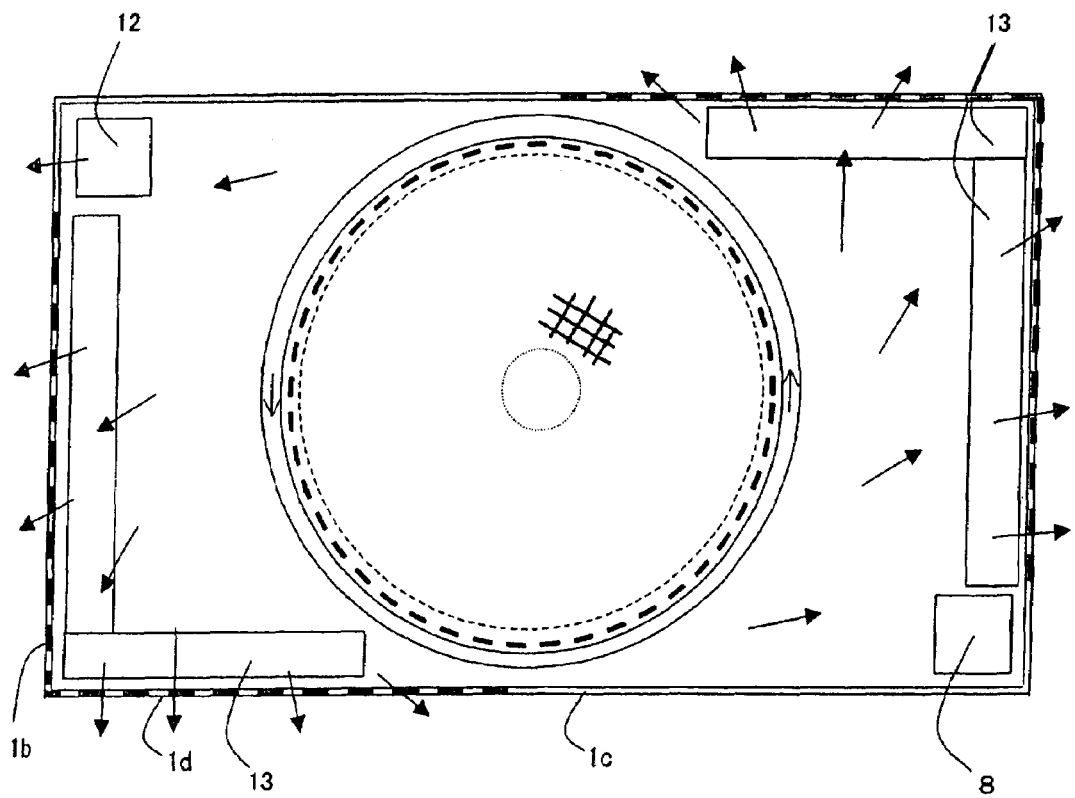
FIG. 30A and FIG. 30B are cross-sectional views showing the construction of a photocatalytic reaction device according to a twenty-ninth embodiment of the present invention.
Figure 30B:
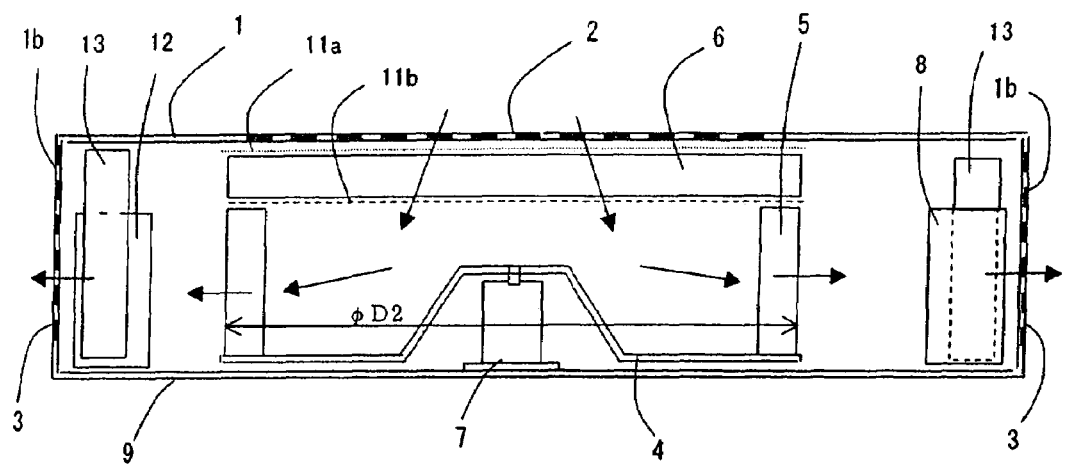

FIG. 30A and FIG. 30B are views showing the construction of a photocatalytic reaction device according to a twenty-ninth embodiment of the present invention.

In the photocatalytic reaction device of this twenty-ninth embodiment, in the photocatalytic reaction device of the twenty-seventh embodiment, ozone decomposition filters 13 are arranged at the outer periphery of the series of vanes 5 of the centrifugal type blower 4.

By thus arranging ozone decomposition filters 13 in for example the vicinity of the discharge ports 3 at the outer periphery of the series of vanes 5 of the centrifugal type blower 4, any ozone generated by the ultraviolet rays that is not employed in decomposition is absorbed by the ozone decomposition filters 13 arranged within the discharge ports 3. As a result, since there is no outflow of excess ozone from the discharge ports 3, sufficient ozone to decompose the impurities in the air can be generated, so that the device according to this embodiment shows a decomposition treatment capability higher than that of the photocatalytic reaction device of the twenty-seventh embodiment. Also, although the series of vanes 5 generates fluid noise, noise is attenuated by the arrangement of the photocatalyst carrier 6 on the side of the intake port 2 and the ozone decomposition filters 13 at the outer periphery, so the noise that is propagated to outside the casing 1 can be reduced.

Thirtieth Embodiment

Figure 31A:
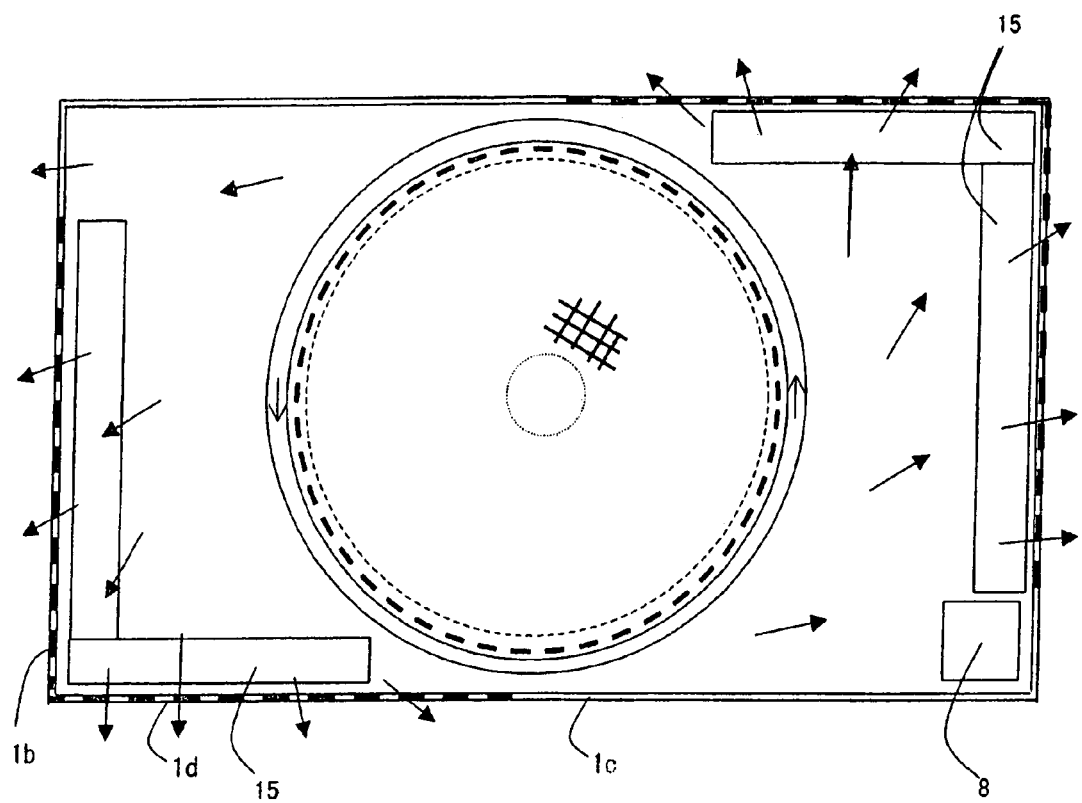
FIG. 31A and FIG. 31B are cross-sectional views showing the construction of a photocatalytic reaction device according to a thirtieth embodiment of the present invention.
Figure 31B:
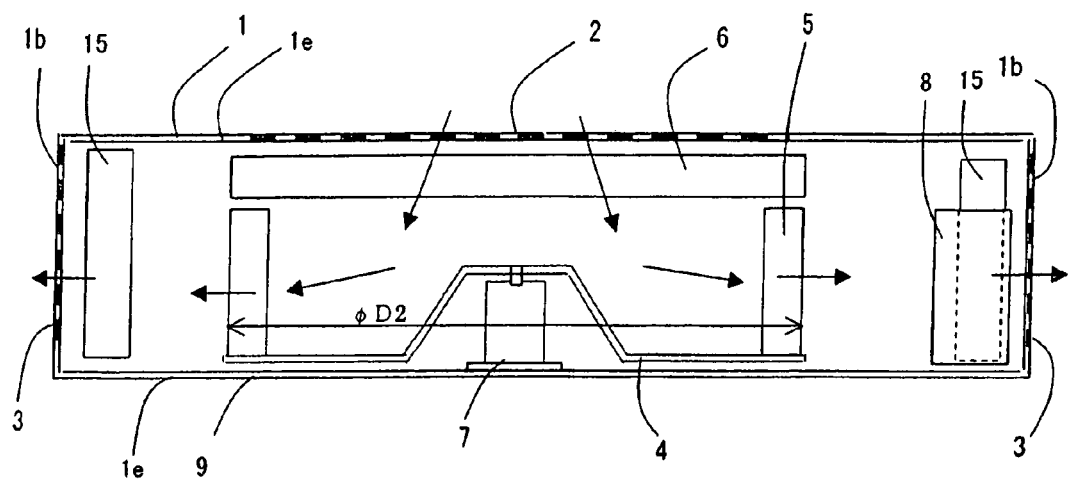

FIG. 31A and FIG. 31B are views showing the construction of a photocatalytic reaction device according to a thirtieth embodiment of the present invention.

In the photocatalytic reaction device according to this thirtieth embodiment, the projection of the casing from a direction perpendicular with respect to the intake port 2 formed in the casing 1 is practically rectangular and the series of vanes 5 of the centrifugal type blower 4 are arranged around the intake port 2 on the inside of the casing, discharge ports 3 being provided at a plurality of locations, for example prescribed locations of the short side face 1b and the long side face 1c, on a side of the casing different from that of the intake port 2; a photocatalyst carrier 6 that carries a visible light reaction type photocatalyst is arranged on the side of the intake port 2 of the series of vanes 5 of the centrifugal type blower 4; deodorizing filters 15 are arranged on the side of the discharge ports 3 of the photocatalyst carrier 6; and the portion (including a mesh-shaped portion of the intake port 2) of the upper surface at the surface of the casing 1 facing the discharge ports 3 on the outlet side of the deodorizing filters 15 and facing the photocatalyst carrier 6 and/or the portion 1e at the periphery thereof are made transparent. It should be noted that the portion facing the photocatalyst carrier 6 or the portion 1e at the periphery thereof of either the upper surface or the lower surface of the casing 1 could be made transparent.

By thus making at least part of the portion facing the photocatalyst carrier 6 of the casing 1 and the portion at the periphery thereof transparent, the photocatalytic reaction is promoted by visible light striking the photocatalyst carrier 6 and high decomposition treatment capability is displayed in respect of impurities in the air.

Also, thanks to the provision of discharge ports 3 in a plurality of locations, the area of the flow path to the discharge ports 3 is increased compared with conventionally, where the discharge port 3 was provided in only a single location and a higher decomposition treatment capability is displayed than conventionally in respect of impurities in the air.

What is claimed is:

1. A photocatalytic reaction device, comprising:
an intake port formed in a casing;
a discharge port formed in a side face of the casing different from said intake port;
a centrifugal blower for feeding fluid flowing in from said intake port to said discharge port;
a photocatalyst carrier carrying photocatalyst and being provided in a fluid path between said intake port and said discharge port, and
a series of vanes of said centrifugal blower provided at an outer periphery of said photocatalyst carrier,
wherein said discharge port is formed over an entire surface of the side face of said casing, and
wherein said photocatalyst carrier is provided around said intake port.

2. A photocatalytic reaction device, comprising:
an intake port formed in a casing;
a discharge port formed in a side face of the casing different from said intake port;
a centrifugal blower for feeding fluid flowing in from said intake port to said discharge port;
a photocatalyst carrier carrying photocatalyst and being provided in a fluid path between said intake port and said discharge port; and
a series of vanes of said centrifugal blower provided at an outer periphery of said photocatalyst carrier,
wherein said discharge port is formed in a plurality of locations of the side face of said casing, and
wherein said photocatalyst carrier is provided around said intake port.

3. A photocatalytic reaction device, comprising:
an intake port formed in a casing;
a discharge port formed in a side face of the casing different from said intake port;
a centrifugal blower for feeding fluid flowing in from said intake port to said discharge port; and
a photocatalyst carrier carrying photocatalyst and being provided in a fluid path between said intake port and said discharge port; and
a series of vanes of said centrifugal blower provided facing a side of said photocatalyst carrier on another side to that of said intake port,
wherein said discharge port is formed over an entire surface of the side face of said casing, and
wherein said photocatalyst carrier is provided facing said intake port.

4. A photocatalytic reaction device, comprising:
an intake port formed in a casing;
a discharge port formed in a side face of the casing different from said intake port;
a centrifugal blower for feeding fluid flowing in from said intake port to said discharge port;
a photocatalyst carrier carrying photocatalyst and being provided in a fluid path between said intake port and said discharge port; and
a series of vanes of said centrifugal blower provided facing a side of said photocatalyst carrier on another side to that of said intake port,
wherein said discharge port is formed in a plurality of locations of the side face of said casing, and
wherein said photocatalyst carrier is provided facing said intake port.

5. A photocatalytic reaction device, comprising:
an intake port formed in a casing;
a discharge port formed in a side face of the casing different from said intake port;
a centrifugal blower for feeding fluid flowing in from said intake port to said discharge port;
a photocatalyst carrier carrying photocatalyst and being provided in a fluid path between said intake port and said discharge port;
a series of vanes of said centrifugal blower provided facing an opposite side of said photocatalyst carrier to that of said intake port; and
a deodorizing filter provided facing said discharge port,
wherein said discharge port is formed over an entire surface of the side face of said casing, and wherein said casing is practically rectangular in projection from a direction perpendicular with respect to said intake port, at least part of a portion of said casing facing said photocatalyst carrier and a periphery thereof is transparent, and said photocatalyst carrier is provided facing said intake port.

6. A photocatalytic reaction device, comprising:

an intake port formed in a casing;

a discharge port formed in a side face of the casing different from said intake port;

a centrifugal blower for feeding fluid flowing in from said intake port to said discharge port;

a photocatalyst carrier carrying photocatalyst and being provided in a fluid path between said intake port and said discharge port;

a series of vanes of said centrifugal blower provided facing an opposite side of said photocatalyst carrier to that of said intake port; and a deodorizing filter provided facing said discharge port, wherein said discharge port is formed in a plurality of locations of the side face of said casing, and wherein said casing is practically rectangular in projection from a direction perpendicular with respect to said intake port, at least part of a portion of said casing facing said photocatalyst carrier and a periphery thereof is transparent, and said photocatalyst carrier is provided facing said intake port.

* * * * *